US008862451B2

(12) United States Patent
Alme et al.

(10) Patent No.: US 8,862,451 B2
(45) Date of Patent: Oct. 14, 2014

(54) USER INTERFACE INDICATING FLUID LOCATION FOR AN IMPLANTABLE FLUID DELIVERY DEVICE

(75) Inventors: Sarah B. Alme, Blaine, MN (US); Touby A. Drew, Golden Valley, MN (US); Jiaying Shen, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 549 days.

(21) Appl. No.: 12/691,574

(22) Filed: Jan. 21, 2010

(65) Prior Publication Data

US 2010/0185182 A1    Jul. 22, 2010

Related U.S. Application Data

(60) Provisional application No. 61/146,529, filed on Jan. 22, 2009.

(51) Int. Cl.
*G06G 7/58* (2006.01)
*G06G 7/48* (2006.01)
*A61M 5/142* (2006.01)
*G09B 23/28* (2006.01)
*G06F 19/00* (2011.01)

(52) U.S. Cl.
CPC ... *A61M 5/14276* (2013.01); *A61M 2205/3507* (2013.01); *A61M 2205/502* (2013.01); *G06F 19/3437* (2013.01); *G09B 23/285* (2013.01); *G06F 19/3468* (2013.01)
USPC ................................................. 703/11; 703/3

(58) Field of Classification Search
USPC .................................................. 703/3, 4, 11
See application file for complete search history.

(56) References Cited

U.S. PATENT DOCUMENTS 5,693,076 A    12/1997  Kaemmerer
5,722,999 A     3/1998  Snell
(Continued)

FOREIGN PATENT DOCUMENTS

EP    1 022 035 A1    7/2000
EP    1 681 069 A1    7/2006
(Continued)

OTHER PUBLICATIONS

Cao et al. "Design and Simulation of an Implantable Medical Drug Delivery System using Microelectromechanical Systems Technology", Elsevier 2001.*

(Continued)

*Primary Examiner* — Saif Alhija
(74) *Attorney, Agent, or Firm* — Shumaker & Sieffert, P.A.

(57) ABSTRACT

A programmer device includes an interface that communicates with an implantable fluid delivery device and a user interface that displays a representation of a portion of the implantable fluid delivery device and displays an indication of a location of fluid within the implantable fluid delivery device during a delivery phase, e.g., a priming or bridging phase. The user interface may display a representation of progress of the delivery phase. The user interface may display the indication of the location of the fluid within internal tubing of the implantable fluid delivery device or within a catheter of the implantable fluid delivery device. The programmer device may display the representation of the progress of the delivery phase as a simulation of the delivery phase or during the actual delivery phase of the implantable fluid delivery device. A user may therefore observe a location of fluid corresponding to progress of the delivery phase.

46 Claims, 30 Drawing Sheets

(56) References Cited

U.S. PATENT DOCUMENTS

| | | |
|---|---|---|
| 5,925,066 A | 7/1999 | Kroll et al. |
| 6,007,493 A | 12/1999 | Ericksen et al. |
| 6,442,433 B1 | 8/2002 | Linberg |
| 6,675,044 B2 | 1/2004 | Chen |
| 7,027,871 B2 | 4/2006 | Burnes et al. |
| 7,047,065 B2 | 5/2006 | Kalgren et al. |
| 7,072,725 B2 | 7/2006 | Bristol et al. |
| 7,347,854 B2 | 3/2008 | Shelton et al. |
| 7,366,570 B2 | 4/2008 | Riff et al. |
| 2001/0012955 A1 | 8/2001 | Goedeke et al. |
| 2001/0047194 A1 | 11/2001 | Thompson et al. |
| 2002/0150872 A1 | 10/2002 | Glenn et al. |
| 2002/0193679 A1 | 12/2002 | Malave et al. |
| 2004/0088020 A1 | 5/2004 | Condie et al. |
| 2004/0181204 A1 | 9/2004 | Jasperson et al. |
| 2005/0043863 A1 | 2/2005 | Ali et al. |
| 2005/0283210 A1 | 12/2005 | Blischak et al. |
| 2006/0041222 A1* | 2/2006 | Dewing et al. ............ 604/93.01 |
| 2006/0206066 A1 | 9/2006 | Ferek-Petric |
| 2006/0272652 A1 | 12/2006 | Stocker et al. |
| 2008/0033402 A1 | 2/2008 | Blomquist |
| 2008/0177254 A1 | 7/2008 | Shelton et al. |
| 2009/0093756 A1 | 4/2009 | Minaie et al. |
| 2011/0253586 A1 | 10/2011 | Metry et al. |
| 2011/0264071 A1 | 10/2011 | Braig et al. |
| 2012/0209241 A1 | 8/2012 | Drew |
| 2013/0274709 A1 | 10/2013 | Shelton et al. |

FOREIGN PATENT DOCUMENTS

| | | |
|---|---|---|
| EP | 1845466 A2 | 10/2007 |
| WO | WO 03/099355 A2 | 12/2003 |
| WO | WO 2005/009514 A2 | 2/2005 |
| WO | WO 2005/107419 A2 | 11/2005 |
| WO | WO 2005107419 A2 * | 11/2005 |
| WO | WO 2009/005957 A1 | 1/2009 |

OTHER PUBLICATIONS

Galanis et al "Computer methods for automating preoperative dental implant planning: Implant positioning and size assignment" Elsevier 2007.*
Notification Concerning International Preliminary Report on Patentability for corresponding patent application No. PCT/US2010/021657, mailed Aug. 4, 2011, 7 pages.
Notification of Transmittal of the International Search Report and the Written Opinion of the International Searching Authority for corresponding patent application No. PCT/US2010/021657, mailed Jul. 7, 2010, 10 pages.
Patent Application entitled, "Display of Supplemental Bolus in Relation to Programmed Dose," U.S. Appl. No. 12/691,513, filed Jan. 21, 2010.
Patent Application entitled, "User Interface That Displays Pending and Selected Programming for an Implantable Medical Device," U.S. Appl. No. 12/691,592, filed Jan. 21, 2010.
Patent Application entitled, "Management of Session History Data for Implantable Fluid Delivery Device," U.S. Appl. No. 12/730,751, filed Mar. 24, 2010.
SynchroMed® II & SynchroMed® EL, Medtronic Reference Card, Bridge Bolus Calculation, Jan. 2008, 2 pages.
SynchroMed® II & SynchroMed® EL, Medtronic Reference Card, Catheter Revision Priming Volume Calculation, Jan. 2008, 2 pages.
SynchroMed® II & SyrichroMed® EL, Medtronic Reference Card, Full Catheter Replacement Priming Volume Calculation, Jan. 2008, 2 pages.
SynchroMed® II & SynchroMed® EL, Medtronic Reference Card, Pump Replacement Priming Volume Calculation, Jan. 2008, 2 pages.
SynchroMed® II, Programmable Infusion System Clinical Reference Guide, Intrathecal Baclofen for the Management of Severe Spasticity, 2007, 56 pages.
SynchroMed® II, Programmable Infusion System Clinical Reference Guide, Intrathecal Morphine for Pain Management, 2007, 54 pages.
SynchroMed® II, Programmable Infusion System Clinical Reference Guide, System Components, 2007, 60 pages.
SynchroMed® II, Programmable Infusion System Clinical Reference Guide, Therapy Maintenance, 2007, 79 pages.
Smart Card Alliance: News, Personal Health Cards Store Life-Saving Medical Information, Speed Up Hospital Administration: From Smart Card Alliance/CTST Conference, May 19, 2008, 2 pages.
Response to Office Action dated Aug. 6, 2013 from U.S. Appl. No. 12/691,513, filed Nov. 6, 2013, 11 pp.
Response to Office Action dated Aug. 6, 2014, from U.S. Appl. No. 12/691,592, filed Nov. 6, 2013, 15 pp.
Final Office Action from U.S. Appl. No. 12/691,513, dated Dec. 24, 2013, 13 pp.
Response to Office Action dated Feb. 5, 2014, from U.S. Appl. No. 12/691,592, filed May 5, 2014, 15 pp.
Notice of Appeal and Pre-Appeal Brief Request for Review from U.S. Appl. No. 12/691,513, filed Mar. 24, 2014, 6 pages.
Response to Office Action dated Dec. 24, 2014, from U.S. Appl. No. 12/691,513, filed Feb. 24, 2014, 9 pp.
Office action for U.S. Appl. No. 12/691,513, dated Mar. 29, 2013, 11 pages.
Office Action from U.S. Appl. No. 12/691,592, dated Feb. 5, 2014, 20 pp.
Response to office action for U.S. Appl. No. 12/691,513, filed Jul. 1, 2013, 14 pages.
Response to office action for U.S. Appl. No. 12/691,592, filed Jul. 15, 2013, 16 pages.
Office action for U.S. Appl. No. 12/691,592, dated Apr. 15, 2013, 15 pages.
Office Action from U.S. Appl. No. 12/691,513, dated Aug. 6, 2013, 9 pp.
Office Action from U.S. Appl. No. 12/691,592, dated Aug. 6, 2013, 17 pp.
Final Office Action from U.S. Appl. No. 12/691,592, dated May 28, 2014, 19 pp.

* cited by examiner

USER INTERFACE INDICATING FLUID LOCATION FOR AN IMPLANTABLE FLUID DELIVERY DEVICE

This application claims the benefit of U.S. Provisional Application No. 61/146,529, filed Jan. 22, 2009, which is hereby incorporated by reference in its entirety.

TECHNICAL FIELD

This disclosure relates to programmers that control programming of implantable medical devices, such as implantable fluid delivery devices.

BACKGROUND

A variety of medical devices are used for chronic, i.e., long-term, delivery of therapy to patients suffering from a variety of conditions, such as chronic pain, tremor, Parkinson's disease, epilepsy, urinary or fecal incontinence, sexual dysfunction, obesity, spasticity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician. The devices may be implantable medical devices that receive the program from a programmer controlled by the clinician.

Examples of such implantable medical devices include implantable fluid delivery devices, implantable neurostimulators, implantable cardioverters, implantable cardiac pacemakers, implantable defibrillators, cochlear implants, and others that now exist or may exist in the future. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device which can deliver a fluid medication to a patient at a selected site. A drug infusion device may be implanted at a location in the body of a patient and deliver a fluid medication through a catheter to a selected delivery site in the body. Drug infusion devices, such as implantable drug pumps, include fluid reservoirs that may be self-sealing and may be accessible through ports. A drug infusion device may be configured to deliver a therapeutic agent from the fluid reservoir to a patient according to a therapy program, which may, for example, specify a rate of delivery by the IMD of a fluid delivered to the patient.

Programmable implantable medical devices are typically programmed using an external programming device, sometimes known as a controller or programmer, which can communicate with the implanted medical device through well known techniques such as wireless telemetry. An external controller, or programmer, can be used by a medical professional, for example, to change the therapeutic regimen by increasing or decreasing the amount of fluid medication delivered to the patient. Typically, a medical professional interfaces with the external controller or programmer to set various parameters associated with the implantable medical device and then transmits, or downloads, those parameters to the implanted medical device. The external device may also record other information important to the delivery of the therapy. Some information may be stored in the implantable medical device and/or the external programming device. Such information may include patient information, implanted device information such as model, volume, implant location, length of catheter or lead, and other information specific to different devices.

SUMMARY

In general, techniques are described for displaying a representation of a delivery phase, such as a priming phase or a bridging phase, of an implantable medical device (IMD), such as an implantable fluid delivery device, an actual or simulated progress of the delivery phase, and a location of a fluid within the IMD during the delivery phase. The display may include a representation of a portion of the IMD, such as a reservoir, internal tubing, and a catheter, each of which may contain portions of one or more fluids delivered by the IMD. The representation may be a graphical representation of at least some of the structure of the IMD. The display of the fluid may depict the fluid in the reservoir, the internal tubing, and/or the catheter, depending on the progress of the delivery phase. The techniques may be applied to simulate a delivery phase of an IMD or during the actual delivery phase of the IMD.

A user of a programmer for programming the IMD may therefore observe an indication of actual or simulated movement of the fluid through the IMD that occurs or is expected to occur during the delivery phase, which may assist the user in properly programming the delivery phase of the IMD. For example, when the delivery phase of the IMD is a priming phase, the user may determine whether a priming bolus has an accurate volume, whether the priming phase is sufficient in duration, or determine whether other factors influencing the priming phase are accurate before the priming phase begins. As another example, when the delivery phase of the IMD is a bridging phase, the user may determine whether the bridging phase will deliver all of an old fluid at an appropriate rate (or pattern of rates) before automatically delivering a new fluid at a different rate (or pattern of rates).

In one example, a method includes displaying a representation of a portion of an implantable fluid delivery device via a user interface associated with a programmer device that communicates with the implantable fluid delivery device and displaying an indication of a location of fluid within the implantable fluid delivery device during a delivery phase via the user interface.

In another example, a programmer device includes a device interface that communicates with an implantable fluid delivery device, and a user interface that displays a representation of a portion of the implantable fluid delivery device and displays an indication of a location of fluid within the implantable fluid delivery device during a delivery phase of the implantable fluid delivery device.

In another example, a system includes an implantable fluid delivery device that delivers a fluid to a patient, and a programmer device, communicatively coupled to the implantable fluid delivery device, that displays a representation of a portion of the implantable fluid delivery device and displays an indication of a location of fluid within the implantable fluid delivery device.

In another example, a computer-readable medium, such as a computer-readable storage medium, contains instructions that cause a programmable processor to display a representation of a portion of an implantable fluid delivery device and display an indication of a location of fluid within the implantable fluid delivery device during a delivery phase of the implantable fluid delivery device.

In another example, a device includes means for displaying a representation of a portion of an implantable fluid delivery device and means for displaying an indication of a location of fluid within the implantable fluid delivery device during a delivery phase.

The details of one or more example aspects of this disclosure are set forth in the accompanying drawings and the description below. Other features, objects, and advantages will be apparent from the description and drawings, and from the claims.

BRIEF DESCRIPTION OF DRAWINGS

FIG. 6 is a screenshot illustrating an example user interface screen presented by an external programmer for editing patient information.

FIG. 7 is a screenshot illustrating an example user interface screen presented by an external programmer for editing fluid delivery pump and catheter information.

FIG. 15 is a screenshot illustrating an example user interface screen presented by an external programmer for entering and changing drug information and/or concentration information.

DETAILED DESCRIPTION

Figure 1:
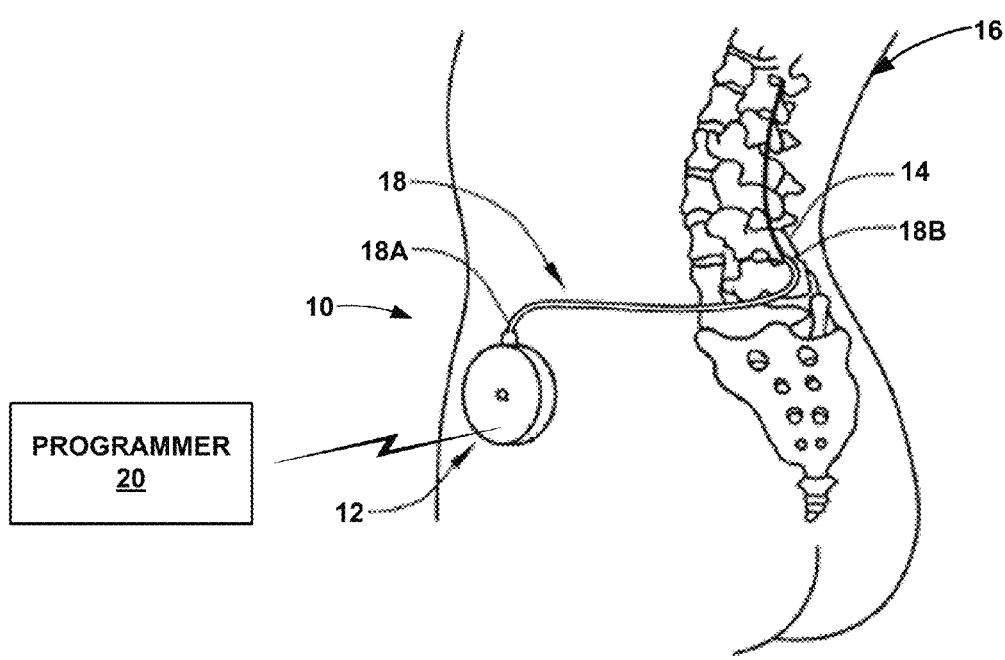
FIG. 1 is a conceptual diagram illustrating an example of a fluid delivery system, which includes an implantable medical device that is configured to deliver a therapeutic agent to a patient via a catheter.

Medical devices are useful for treating, managing or otherwise controlling various patient conditions or disorders, such as, but not limited to, pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical devices may be configured to deliver one or more therapeutic agents, alone or in combination with other therapies, such as electrical stimulation, to one or more target sites within a patient. For example, in some cases, a medical device may deliver one or more pain-relieving drugs to patients with chronic pain, insulin to a patient with diabetes, or other fluids to patients with different disorders. The medical device may be implanted in the patient for chronic therapy delivery (e.g., longer than a temporary, trial basis) or temporary delivery.

As used in this disclosure, the term dosing program generally refers to a program sent to an implantable fluid delivery device by a device for programming the implantable fluid delivery device to cause the implantable fluid delivery device to deliver fluid at a certain rate at a certain time. The dosing program may include, for example, definitions of a priming bolus, a bridging phase, a supplemental bolus, and a therapy schedule. A dosing program may include additional information, such as patient information, permissions for a user to add a supplemental bolus, historical therapy schedules, fluid or drug information, or other information. The term therapy schedule may generally refer to a rate (which may be zero) at which to administer fluid, or a drug or drug combination within the fluid, at specific times to a patient. In particular, the therapy schedule may define one or more programmed doses, which may be periodic or aperiodic, each dose including a rate of fluid delivery and a time duration for which to deliver the dose. Dose generally refers to the amount of drug delivered over a period of time, and may change over the course of a therapy schedule such that a drug may be delivered at different rates at different times.

A priming bolus refers to a bolus delivered by the implantable fluid delivery device to move the fluid to the distal tip of the catheter, i.e., the tip of the catheter that is remote from the reservoir and internal tubing, if applicable. Once the fluid is primed to the distal tip of the catheter, the IMD is ready to deliver fluid to the patient from the distal tip, e.g., via one or more fluid outlets at or near the distal tip. The device delivers the priming bolus during a priming phase to prepare the device for delivery of the fluid to the patient. An implantable fluid delivery device also may perform a bridge when a new fluid is inserted into a reservoir of the device while an old fluid is still present in the device, e.g., within internal tubing of the device and/or within a catheter connected to the device. The bridge is performed to define a rate at which to deliver the old fluid until the old fluid is completely delivered out of the catheter and to the patient such that the device contains only the new fluid. A supplemental bolus is a bolus administered to the patient outside of the therapy schedule. The terms independent bolus, one-time bolus, and therapeutic bolus may also be used in this disclosure to refer to a supplemental bolus. In one example, the implantable fluid delivery device may administer a supplemental bolus before the implantable fluid delivery device begins administering doses of fluid according to the therapy schedule. In another example, the implantable fluid delivery device may administer a supplemental bolus during the therapy schedule, e.g., to override or supplement the therapy schedule in response to clinician instruction or patient request.

In accordance with various techniques described in this disclosure, a programmer device that programs an implantable fluid delivery device may display a representation of a portion of an implantable fluid delivery device via a user interface and simultaneously display an indication of a location of fluid within the implantable fluid delivery device during a delivery phase via the user interface. In general, a delivery phase of an implantable fluid delivery device may comprise a phase of the device during which a fluid is moved toward a distal tip of a catheter of the device. The delivery phase may comprise, for example, a priming phase or a bridging phase of the implantable fluid delivery pump. During a priming phase, the fluid is moved to the catheter tip, thereby filling the catheter in preparation for delivery of fluid from the catheter to the patient. During a bridging phase, an old fluid is expelled at a rate appropriate for the old fluid, and a new fluid is moved to the catheter tip as the old fluid is expelled. Once the old fluid has been expelled and the new fluid has reached the catheter tip, the device may begin delivering fluid according to a dosing program appropriate for the new fluid. The programmer device may display the representations of drug location at various times, e.g., during an actual delivery phase of the implantable fluid delivery device or during a simulation of the fluid delivery phase. Presenting fluid location during a simulation may help the clinician visualize the progress of a priming or bridging phase and verify that the size of a priming or bridging bolus is appropriate to achieve the desired result.

FIG. 1 is a conceptual diagram illustrating an example of a therapy system 10, which includes implantable medical device (IMD) 12 configured to deliver at least one therapeutic agent, such as a pharmaceutical agent, insulin, pain relieving agent, anti-inflammatory agent, gene therapy agent, or the like, to a target site within patient 16 via catheter 18, which is coupled to IMD 12. In one example, catheter 18 may comprise a plurality of catheter segments. In other examples, catheter 18 may be a unitary catheter. In the example of FIG. 1, the therapeutic agent is a therapeutic fluid. IMD 12 may be, for example, an implantable fluid delivery device that delivers therapeutic agents in fluid form to patient 16. In the example shown in FIG. 1, the target site is proximate to spinal cord 14 of patient 16. A proximal end 18A of catheter 18 is coupled to IMD 12, while a distal end 18B of catheter 18 is located proximate to the target site. Therapy system 10 also includes external programmer 20, which wirelessly communicates with IMD 12 as needed, such as to provide or retrieve therapy information or control aspects of therapy delivery (e.g., modify the therapy parameters, turn IMD 12 on or off, and so forth). Programmer 20 may include a user interface that may display a representation of a portion of an implantable fluid delivery device and simultaneously displays an indication of a location of fluid within the implantable fluid delivery device during an actual or simulated delivery phase, as discussed in greater detail below. While patient 16 is generally referred to as a human patient, other mammalian or non-mammalian patients are also contemplated.

Generally, IMD 12 has an outer housing that is constructed of a biocompatible material that resists corrosion and degradation from bodily fluids, such as titanium or biologically inert polymers. IMD 12 may be implanted within a subcutaneous pocket close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spine 14. Catheter 18 is positioned such that one or more fluid delivery outlets of catheter 18 are proximate to the one or more targets within patient 16. IMD 12 delivers a therapeutic agent to the one or more targets proximate to spinal cord 14 with the aid of catheter 18. For example, IMD 12 may be configured for intrathecal drug delivery into the intrathecal space or epidural space surrounding spinal cord 14. The intrathecal space is within the subarachnoid space of spinal cord 14, which is past the epidural space and dura mater and through the theca of spinal cord 14.

Therapy system 10 may be used, for example, to reduce pain experienced by patient 16. IMD 12 may deliver one or more therapeutic agents to patient 16 according to one or more dosing programs that set forth different therapy parameters, such as a therapy schedule specifying programmed doses, dose rates for the programmed doses, and specific times to deliver the programmed doses. In some examples, the therapeutic agent may be a liquid. The dosing programs may be a part of a program group for therapy, where the group includes a plurality of dosing programs and/or therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. Patient 16 may select and/or generate additional dosing programs for use by IMD 12 via external programmer 20 at any time during therapy or as designated by the clinician.

In some examples, multiple catheters 18 may be coupled to IMD 12 to target the same or different tissue or nerve sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 16 to view and modify therapy parameters. The clinician programmer may include additional or alternative programming features than the patient programmer. For example, more complex or sensitive tasks may only be allowed by the clinician programmer to prevent patient 16 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 18, the position of catheter 18 within patient 16, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

The clinician uses programmer 20 to program IMD 12 with one or more therapy programs that define the therapy delivered by IMD 12. During a programming session, the clinician may determine one or more dosing programs that may provide effective therapy to patient 16. Patient 16 may provide feedback to the clinician as to the efficacy of a specific program being evaluated or desired modifications to the dosing program. Once the clinician has identified one or more programs that may be beneficial to patient 16, patient 16 may continue the evaluation process and determine which dosing program or therapy schedule best alleviates the condition of patient 16 or otherwise provides efficacious therapy to patient 16. The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental boluses such as patient-initiated boluses (e.g., a lock-out interval), a maximum dose that may be delivered over a given time interval, and so forth. IMD 12 may include a feature that prevents dosing the therapeutic agent in a manner inconsistent with the dosing program. Programmer 20 may assist the clinician in the creation/identification of dosing programs by providing a methodical system of identifying potentially beneficial therapy parameters.

A dosage of a therapeutic agent, such as a drug, may be expressed as an amount of drug, e.g., measured in milligrams, provided to the patient over a particular time interval, e.g., per day or twenty-four hour period. This dosage amount may convey to the caregiver an indication of the probable efficacy of the drug and the possibility of side effects of the drug. In general, a sufficient amount of the drug should be administered in order to have a desired therapeutic effect, such as pain relief. However, the amount of the drug administered to the patient should be limited to a maximum amount, such as a maximum daily dose, in order not to avoid potential side effects. Program information specified by a user via programmer 20 may be used to control dosage amount, dosage rate, dosage time, maximum dose for a given time interval (e.g., daily), or other parameters associated with delivery of a drug or other fluid by IMD 12.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 12 and another programmer via remote telemetry techniques known in the art, communicating via a local area network (LAN), wide area network (WAN), public switched telephone network (PSTN), or cellular telephone network, for example.

In other applications of therapy system 10, the target therapy delivery site within patient 16 may be a location proximate to sacral nerves (e.g., the S2, S3, or S4 sacral nerves) in patient 16 or any other suitable nerve, organ, muscle or muscle group in patient 16, which may be selected based on, for example, a patient condition. For example, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. As further examples, catheter 18 may be positioned to deliver a therapeutic agent to help manage peripheral neuropathy or post-operative pain mitigation, ilioinguinal nerve therapy, intercostal nerve therapy, gastric stimulation for the treatment of gastric motility disorders and/or obesity, muscle stimulation, for mitigation of other peripheral and localized pain (e.g., leg pain or back pain). As another example, catheter 18 may be positioned to deliver a therapeutic agent to a deep brain site or within the heart (e.g., intraventricular delivery of the agent). Delivery of a therapeutic agent within the brain may help manage any number of disorders or diseases. Example disorders may include depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

Examples of therapeutic agents that IMD 12 may be configured to deliver include, but are not limited to, insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics.

In accordance with the techniques described herein, programmer 20 may depict a representation of a priming phase of IMD 12 to a user, such as a clinician, doctor, patient, or other user, e.g., with a user interface of programmer 20. That is, a user interface of programmer 20 may present a representation of the progress of the priming phase of IMD 12, display a representation of a portion of IMD 12, and display an indication of a location of fluid within IMD 12 during the course of the priming phase. In particular, the user interface of programmer 20 may provide a representation of the position to which fluid has flowed during the progression of the priming phase. A priming phase may generally refer to a delivery phase during which fluid is moved toward the distal tip of the catheter. Depending on the structure of the IMD, the priming phase may involve delivery of fluid from the reservoir, through internal tubing coupled to the reservoir, and to the tip of a catheter coupled to the tubing, such that the fluid is in a position to be infused into the patient when desired. The representation of progress of the priming phase may be, for example, a status indicator moving along a timeline. Programmer 20 may also overlay the indication of the location of the fluid with the displayed portion of IMD 12 such that the display indicates the location of fluid within the representation of IMD 12. For example, programmer 20 may depict the fluid as being present at various positions within a reservoir of IMD 12, within internal tubing of IMD 12, or within catheter 18 of IMD 12. Programmer 20 may present these representations as a simulation of the priming phase, or during the actual priming phase, of IMD 12.

Programmer 20 may also display similar representations for a bridging phase of IMD 12, e.g., when a new drug is inserted into IMD 12 while an old drug is still present within IMD 12, in which case the old drug may be expelled from the catheter and internal tubing in a controlled manner and at a safe rate to begin delivery of a new drug at a rate appropriate for the second drug. That is, programmer 20 may program IMD 12 to deliver the old drug at one rate or according to one dosing program and to deliver the new drug according to a different dosing program, where the new drug follows delivery of the old drug. Moreover, programmer 20 may program IMD 12 to automatically switch to the new dosing program when all of the old drug has been delivered to patient 16. In one example, programmer 20 programs IMD 12 to deliver the old drug until IMD 12 has delivered a volume of fluid that is equal to the volume of the fluid containing the old fluid. IMD 12 and/or programmer 20 may determine the volume of a fluid delivered by calculating, with processor 38 or processor 84 respectively, the rate(s) at which fluid is delivered and the time during which fluid is delivered at the particular rate.

Figure 2:
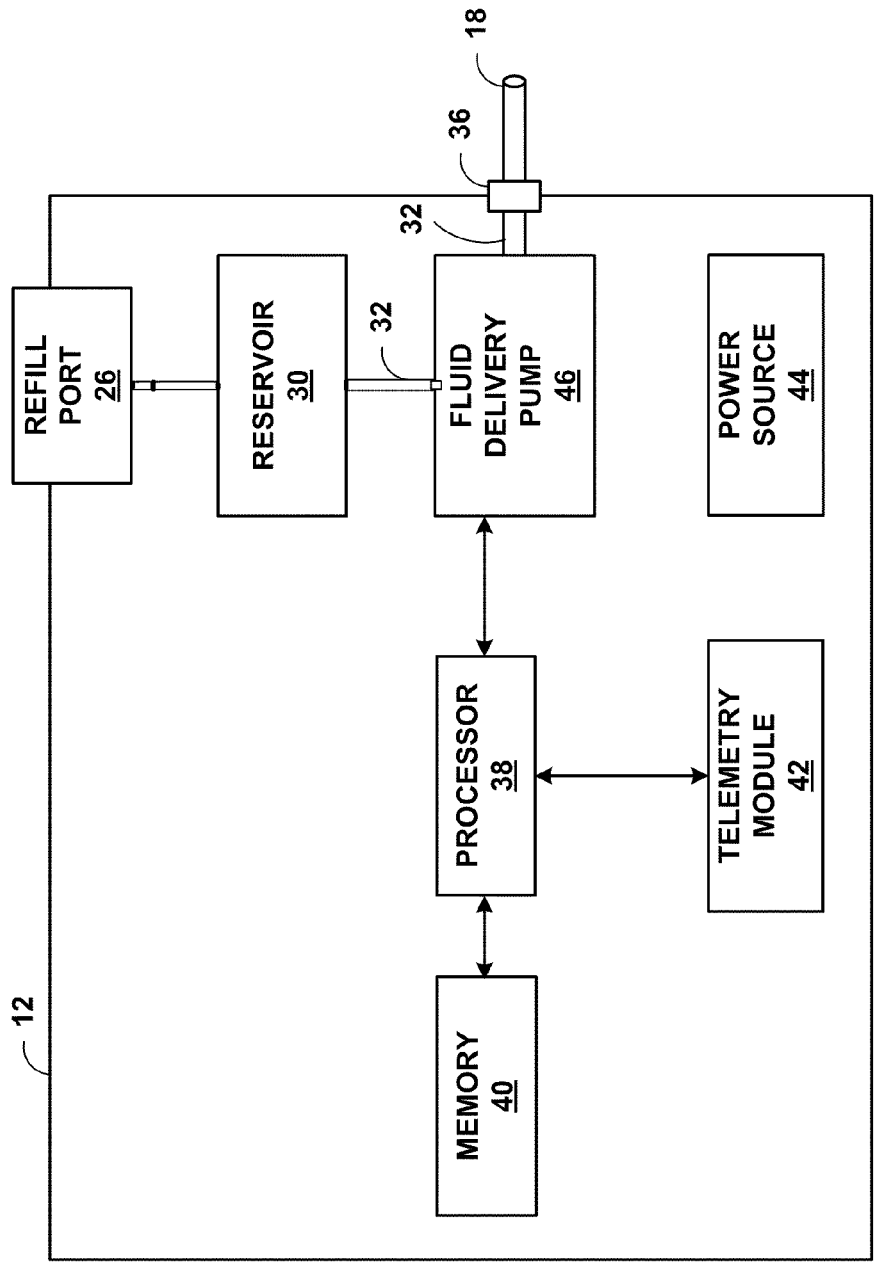
FIG. 2 is functional block diagram illustrating an example of an implantable fluid delivery device.

FIG. 2 is a functional block diagram illustrating components of an example of IMD 12, which includes refill port 26, reservoir 30, processor 38, memory 40, telemetry module 42, power source 44, fluid delivery pump 46, internal tubing 32, and catheter access port 36. Fluid delivery pump 46 may be a mechanism that delivers a therapeutic agent in some metered or other desired flow dosage to the therapy site within patient 16 from reservoir 30 via the catheter 18. Refill port 26 may comprise a self-sealing membrane to prevent loss of therapeutic agent delivered to reservoir 30 via refill port 26. After a delivery system, e.g., a hypodermic needle, penetrates the membrane of refill port 26, the membrane may seal shut when the needle is removed from refill port 26.

Internal tubing 32 is a segment of tubing that runs from reservoir 30, around or through fluid delivery pump 46 to catheter access port 36. In one example, fluid delivery pump 46 may be a squeeze pump that squeezes internal tubing 32 in a controlled manner, e.g., such as a peristaltic pump, to progressively move fluid from reservoir 30 to the distal end of catheter 18 and then into the patient according to parameters specified by a set of program information. Fluid delivery pump 46 may, in other examples, comprise a an axial pump, a centrifugal pump, a pusher plate, a piston-driven pump, or other means for moving fluid through internal tubing 32 and catheter 18.

Processor 38 controls the operation of fluid delivery pump 46 with the aid of instructions associated with program information that is stored in memory 40. For example, the instructions may define dosing programs that specify the amount of a therapeutic agent that is delivered to a target tissue site within patient 16 from reservoir 30 via catheter 18. The instructions may further specify the time at which the agent will be delivered and the time interval over which the agent will be delivered. The amount of the agent and the time over which the agent will be delivered are a function of the dosage rate at which the fluid is delivered. The therapy programs may also include other therapy parameters, such as the frequency of bolus delivery, the type of therapeutic agent delivered if IMD 12 is configured to deliver more than one type of therapeutic agent), and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 40 may include any volatile or non-volatile media, such as a random access memory (RAM), read only memory (ROM), non-volatile RAM (NVRAM), electrically erasable programmable ROM (EEPROM), flash memory, and the like. As mentioned above, memory 40 may store program information including instructions for execution by processor 38, such as, but not limited to, therapy programs, historical therapy programs, timing programs for delivery of fluid from reservoir 30 to catheter 18, and any other information regarding therapy of patient 16. A program may indicate the bolus size or flow rate of the drug, and processor 38 may accordingly deliver therapy. Memory 40 may include separate memories for storing instructions, patient information, therapy parameters (e.g., grouped into sets referred to as "dosing programs"), therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 40 stores program instructions that, when executed by processor 38, cause IMD 12 and processor 38 to perform the functions attributed to them in this disclosure.

Telemetry module 42 in IMD 12, as well as telemetry modules in other devices described herein, such as programmer 20, may accomplish communication by RF communication techniques. In addition, telemetry module 42 may communicate with programmer 20 via proximal inductive interaction of IMD 12 with external programmer 20. Accordingly, telemetry module 42 may send information to external programmer 20 on a continuous basis, at periodic intervals, or upon request from the programmer. Processor 38 controls telemetry module 42 to send and receive information. Wireless telemetry may be accomplished by RF communication or proximal inductive interaction of IMD 12 with external programmer 20.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As a further alternative, an external inductive power supply could transcutaneously power IMD 12 whenever measurements are needed or desired.

Figure 3:
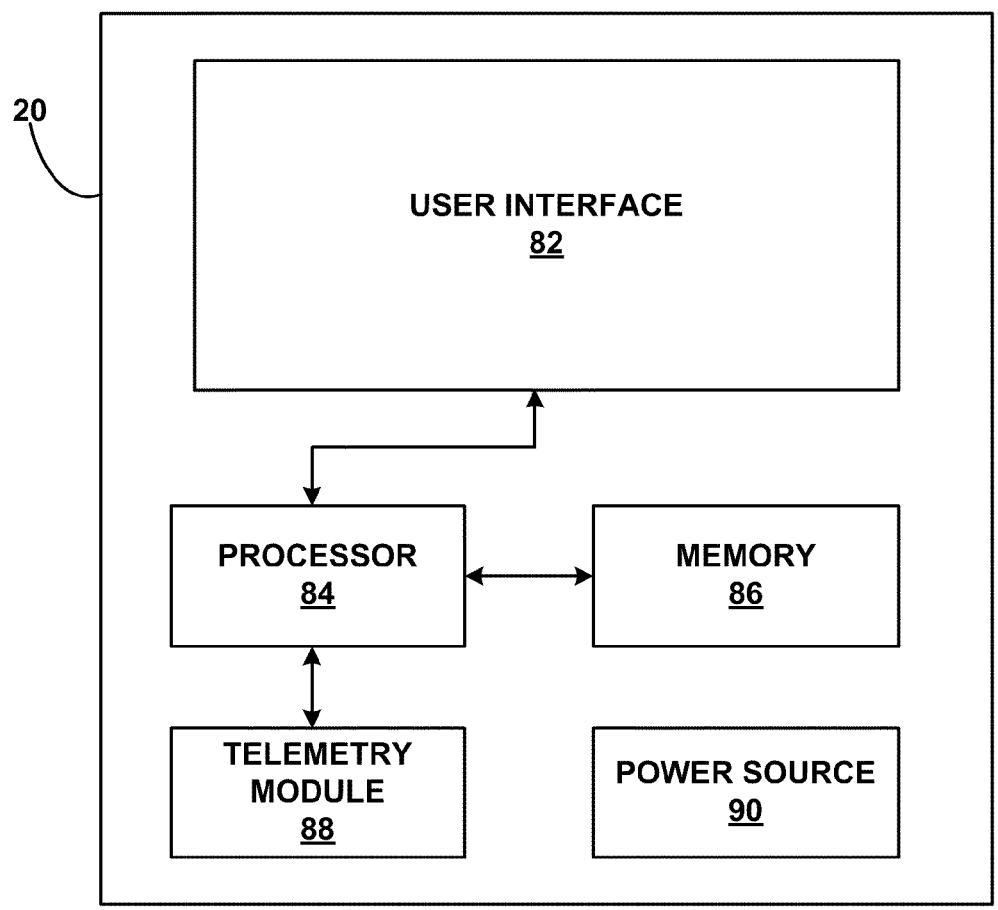
FIG. 3 is a functional block diagram illustrating example components of an external programmer for an implantable medical device.

FIG. 3 is a functional block diagram illustrating various components of an external programmer 20 for IMD 12. As shown in FIG. 3, external programmer 20 includes processor 84, memory 86, telemetry module 88, user interface 82, and power source 90. A clinician or patient 16 interacts with user interface 82 in order to manually change the parameters of a dosing program, change dosing programs within a group of programs, view therapy information, view historical therapy regimens, establish new therapy regimens, or otherwise communicate with IMD 12 or view programming information.

User interface 82 may include a screen and one or more input buttons, as discussed in greater detail below, that allow external programmer 20 to receive input from a user. Alternatively, user interface 82 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

Input buttons for user interface 82 may include a touch pad, increase and decrease buttons, emergency shut off button, and other buttons needed to control the therapy, as described above with regard to patient programmer 20. Processor 84 controls user interface 82, retrieves data from memory 86 and stores data within memory 86. Processor 84 also controls the transmission of data through telemetry module 88 to IMD 12. The transmitted data may include therapy program information specifying various drug delivery program parameters. Memory 86 may include operational instructions for processor 84 and data related to therapy for patient 16.

User interface 82 may be configured to present therapy program information to the user. User interface 82 enables a user to program IMD 12 in accordance with one or more dosing programs, therapy schedules, or the like. As discussed in greater detail below, a user such as a clinician, physician or other caregiver may input patient information, drug information, therapy schedules, priming information, bridging information, drug/IMD implant location information, or other information to programmer 20 via user interface 82. In addition, user interface 82 may display therapy program information as graphical bar graphs or charts, numerical spread sheets, or in any other manner in which information may be displayed. Further, user interface 82 may present nominal or suggested therapy parameters that the user may accept via user interface 82.

User interface 82 may be configured to display a location of IMD 12 within patient 16, as well as a location of fluid within IMD 12. User interface 82 may display a representation of the location of the fluid overlaid with a representation of IMD 12. The representation may be a graphical representation. In some cases, the graphical representation may be a pictorial representation. As described in greater detail herein, user interface 82 may display a representation of progress of a delivery phase of IMD 12. User interface 82 may simultaneously display a representation of fluid corresponding to the represented progress of the delivery phase at a location within IMD 12. For example, user interface 82 may indicate the location of the fluid within IMD 12 at the time corresponding to the progress of the delivery phase. User interface 82 may present a picture of a portion of IMD 12, and present an indication of a location of fluid within the picture IMD 12 corresponding to the delivery phase of IMD 12.

In some examples, the location may be indicated, in part, by the position of the distal-most portion of the fluid column defined by the fluid extending toward the distal end of the catheter 18 within IMD 12. User interface 82 may display a representation of the delivery phase as a simulation or during the actual delivery phase of IMD 12. As one example, and as further discussed with respect to, e.g., FIGS. 12A-12C, user interface 82 may display a representation of a reservoir, internal tubing, and a catheter of IMD 12, and display the location of the fluid during the priming phase as being in the reservoir, the internal tubing, and/or the catheter of IMD 12. The therapy program information may also be stored within memory 86 periodically during therapy, whenever external programmer 20 communicates within IMD 12, or only when the user desires to use or update the therapy program information.

Telemetry module 88 allows the transfer of data to and from IMD 12. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Power source 90 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12. The techniques described in this disclosure may be communicated between IMD 12 via any type of external device capable of communication with IMD 12.

External programmer 20 is one example of a programmer device that includes a device interface that communicates with an implantable fluid delivery device and a user interface that displays a representation of a portion of the implantable fluid delivery device and displays an indication of a location of fluid within the implantable fluid delivery device during a delivery phase of the implantable fluid delivery device.

Figure 4:
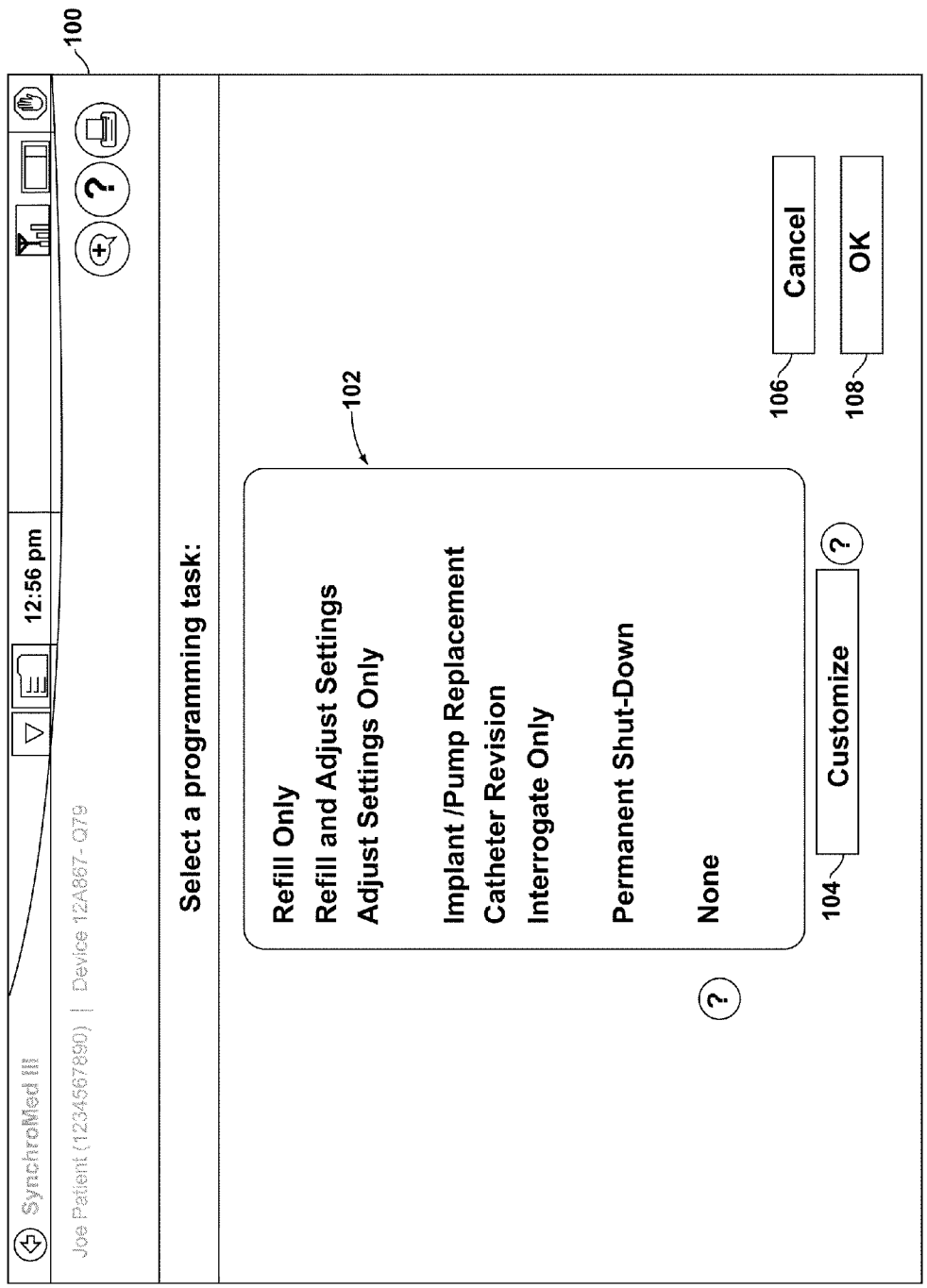
FIG. 4 is a screenshot illustrating an example user interface screen presented by an external programmer when a user first begins interacting with the programmer.

FIG. 4 is a screenshot illustrating an example user interface screen 100 presented by programmer 20 when a user first begins interacting with programmer 20. User interface screen 100 may be displayed by user interface 82 of programmer 20, and may present a task-oriented programming interface. When a user begins a session of working with programmer 20, programmer 20 presents user interface screen 100 to the user via user interface 82. The user may select from a variety of tasks 102 to perform using programmer 20. Tasks 102 of FIG. 4 depict example tasks "refill only," "refill and adjust settings," "adjust settings only," "implant/pump replacement," "catheter revision," "interrogate only," "permanent shut-down," and "none." Other examples may include additional or fewer tasks for the user to perform. In one example, processor 84 determines, from the selection of tasks 102, a series of task screens to present to the user of programmer 20 via user interface 82. Processor 84 may cause user interface 82 to present one or more task screens, each of which may receive one or more pieces of data from the user, in order to program IMD 12 according to the selected one of tasks 102. Programmer 20 may implement more task screens than are necessary for any one of tasks 102, therefore programmer 20 may not display unnecessary screens to the user. In this manner, programmer 20 may assist a user in efficiently programming IMD 12 by requesting relevant data without requesting unnecessary data. Programmer 20 may therefore minimize the number of screens that are displayed based on a selection from tasks 102.

The user may select one of tasks 102 from screen 100. For example, the user may select one of the tasks using a pointer controlled by a mouse or other pointing device. As another example, the user may select one of the tasks by touching the task on a touch-screen interface, e.g., with a finger or a stylus. The user may select Cancel button 106 to end the current session or, after selecting one of tasks 102, the user may select OK button 108 to perform the task. Upon receiving a selection of OK button 108, the user interface presents a different display screen to enable the user to perform the task with programmer 20. The user may also select Customize button 104 to customize the task selected from list 102, e.g., one or more parts or sub-parts of the task selected from list 102. In this manner, the user may select which of the one or more task screens are displayed.

Figure 5A:
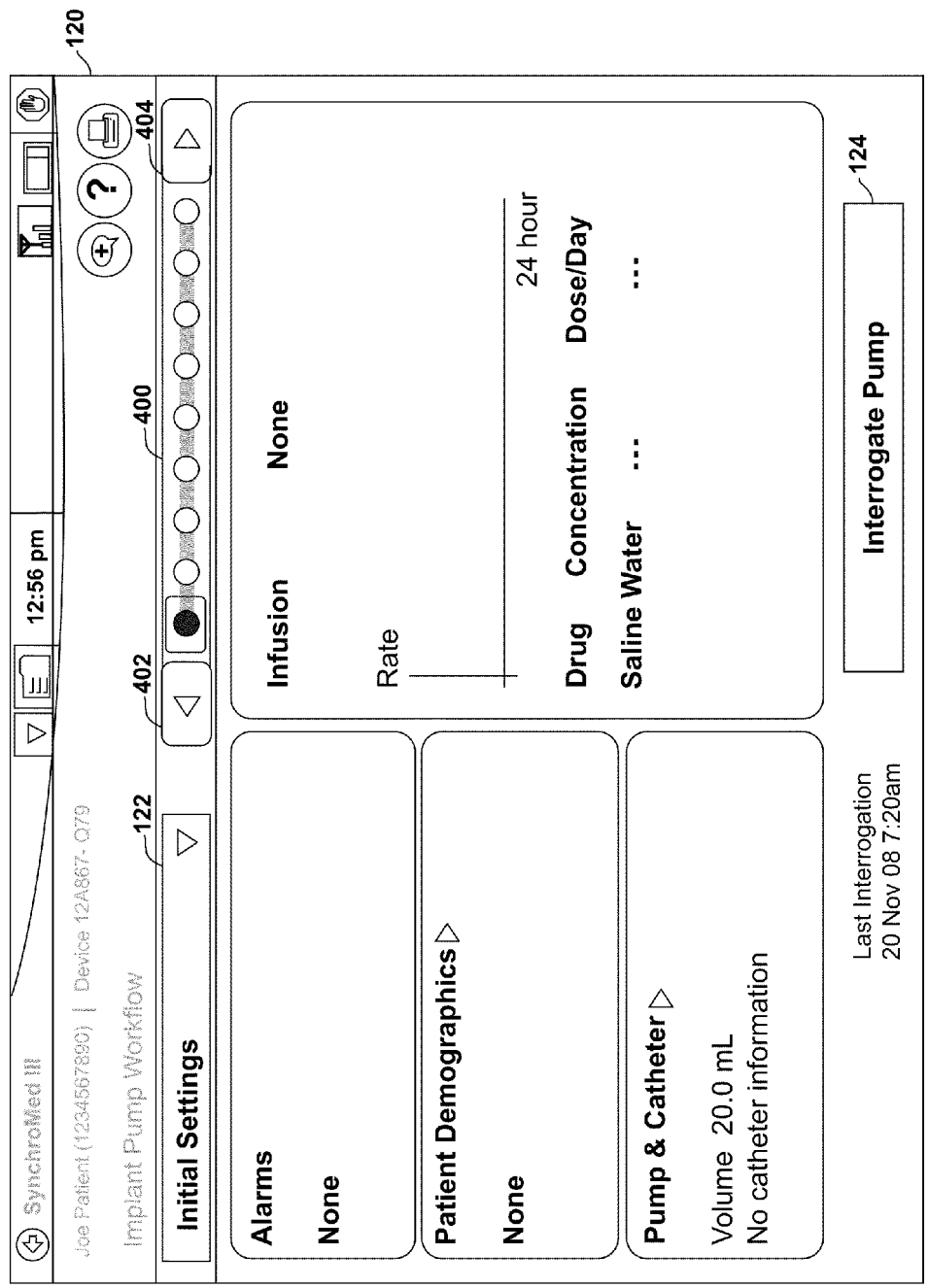
FIGS. 5A and 5B are screenshots illustrating an example user interface screen presented by an external programmer for configuring an implantable medical device.
Figure 5B:
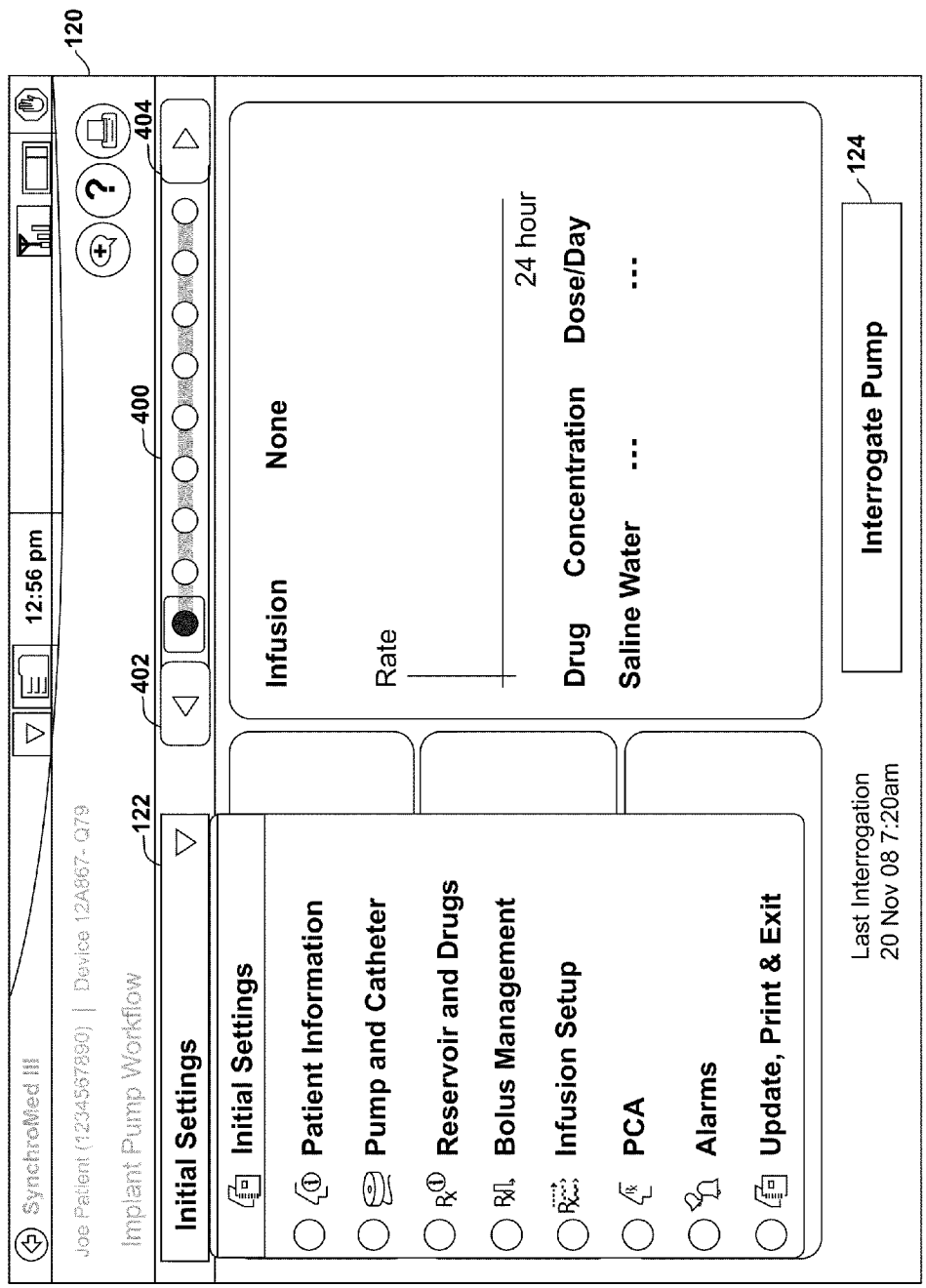

FIGS. 5A and 5B are screenshots illustrating an example user interface screen 120 for configuring IMD 12. User interface screen 120 may be displayed by user interface 82 of programmer 20. User interface screen 120 may be displayed, e.g., when a user selects the "implant/pump replacement" task from tasks 102 and then selects OK button 108 of user interface 100 (FIG. 4). FIG. 5A depicts current therapy program information for the current settings of an IMD, such as IMD 12, associated with the program. For example, the therapy program information may include alarms information, patient demographics information, pump and catheter information, drug information, and an infusion pattern in the example of FIG. 5A. In the example of FIG. 5A, there is no pertinent alarm information or patient demographics information. However, the pump and catheter information indicates that the pump has a volume of 20.0 milliliters (mL). The infusion pattern shows a rate of infusion over a 24 hour period, but is blank in the example of FIG. 5A. The user may select Interrogate Pump button 124 to populate programmer 20 with data stored on IMD 12. The user may elect to do this when IMD 12 has current patient data, but programmer 20 does not. For example, IMD 12 may have been programmed with a different programmer than programmer 20. The user may also select Interrogate Pump button 124 to retrieve data from IMD 12 that IMD 12 has collected during operation within patient 16.

The user may edit settings of the therapy program information by selecting various options from drop-down menu 122 (FIGS. 5A and 5B). FIG. 5B illustrates the options available in this example, which include "initial settings," "patient information," "pump and catheter," "reservoir and drugs," "bolus management," "infusion setup," "PCA," "alarms," and "update, print, and exit." When a user selects any of these options from drop-down menu 122, programmer 20 updates and refreshes user interface screen 120 to illustrate settings and options for the selected option, as discussed in greater detail below.

FIGS. 5A and 5B also include programming status indicator 400, left navigation arrow 402, and right navigation arrow 404. Programming status indicator 400 informs the user of where the user is in the programming process, e.g., in the process of developing a pending dosing program for IMD 12. Processor 84 may, according to instructions encoded within memory 86 of programmer 20, determine which screens are necessary to program IMD 12 based on input received with the example user interface screen of FIG. 4. The user may also navigate between screens using left navigation arrow 402 and right navigation arrow 404. In addition, the user may jump to a particular screen by selecting the screen from drop-down menu 122. When the user selects left navigation arrow 402, processor 84 may cause user interface screen 120 to display a previous screen in the process of programming IMD 12. Similarly, when the user selects right navigation arrow 404, processor 84 may cause user interface screen 120 to display a next screen in the process of programming IMD 12. Status indicator 400 may indicate whether the user has entered sufficient information in each screen, which screen the user is currently viewing, how many screens are remaining, or other information regarding the programming status of IMD 12.

Figure 6:
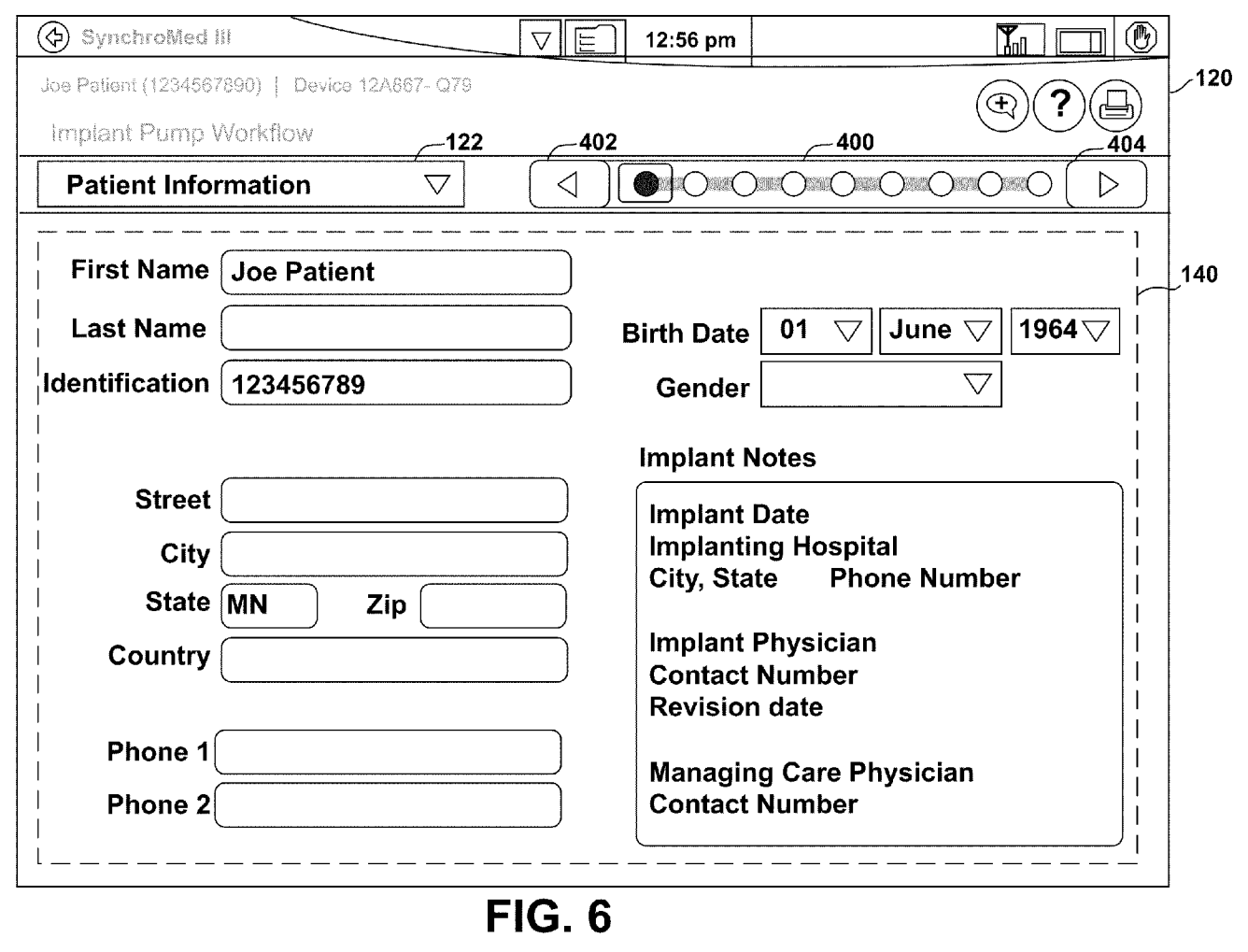

FIG. 6 is a screenshot illustrating an example user interface screen 120 for editing patient information 140, e.g., upon selection of "patient information" from drop-down menu 122 (FIG. 5B). User interface screen 120 displays patient information 140 when a user selects "patient information" from drop-down menu 122. The user may fill in fields of patient information 140 to save patient data to memory 86 of programmer 20, such that the patient information can be retrieved at a later time. This information may also assist the user in selecting a therapy regimen for patient 16. As shown in FIG. 6, the patient information 140 may include a variety of information, such as name, gender, address, identification number, and birth date, as well as various implant notes that may be recorded by a clinician with respect to the implant date, site, and physician for a particular patient.

Figure 7:
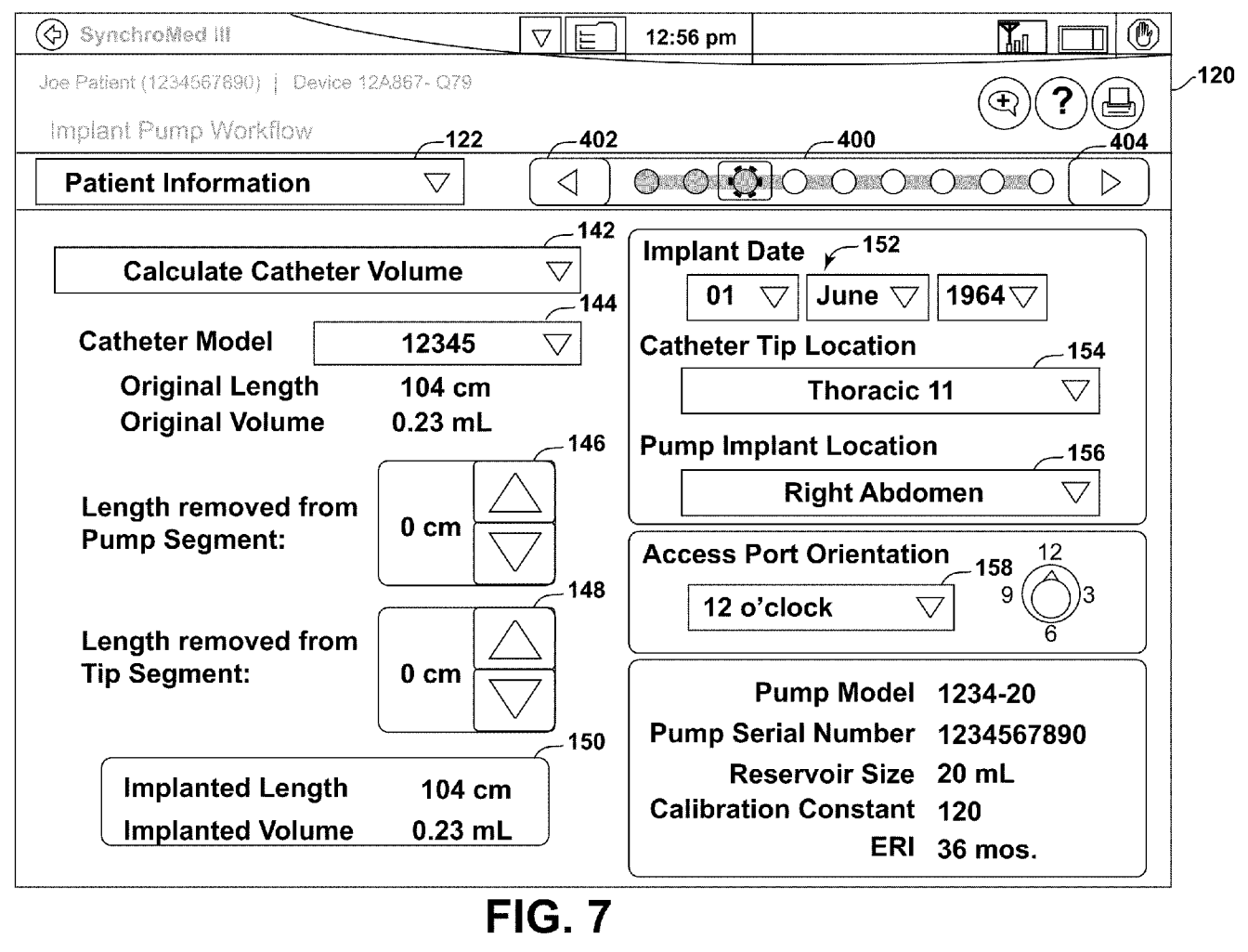

FIG. 7 is a screenshot illustrating an example user interface screen 120 for editing information relating to the fluid delivery pump and catheter implanted in a patient. User interface screen 120 displays information for editing fluid delivery pump and catheter information when the user selects "pump and catheter" from drop-down menu 122. For example, user interface screen 120 enables a user to describe catheter volume, a date of implantation of IMD 12, a location of IMD 12, and other information regarding IMD 12.

The user can select various methods for entering catheter volume from catheter volume drop-down menu 142. In the example of FIG. 7, the user has selected "calculate catheter volume," which causes programmer 20 to calculate the catheter volume from various data regarding the catheter. In another example, the user may select "enter catheter volume" from drop-down menu 142, e.g., when the user knows the volume of the catheter and desires to enter the volume directly, rather than having programmer 20 calculate the volume. In the example of FIG. 7, the user selects a catheter model from catheter model drop-down menu 144. Programmer 20 stores default values for potential catheter models for the catheter's length and volume before the catheter has been modified.

When fluid delivery pump IMDs are implanted in patients, surgeons commonly remove one or more segments from the catheter of the IMD in order to properly size the catheter for implantation. To determine a proper bolus amount for priming, the surgeon who removed this segment from the IMD must record the length of the segment removed. The user of programmer 20 may therefore enter the length of the segment removed from the catheter using user interface screen 120 by selecting the length removed from the pump segment with arrows 146 and the length removed from the tip segment with arrows 148. When user interface screen 120 receives removed-length data from arrows 146 and 148, user interface screen 120 sends the data to processor 84, which calculates a resulting length for the catheter, as well as a resulting volume for the catheter, e.g., in accordance with a program or module stored in memory 86. The processor 84 then returns the results to be displayed on user interface screen 120, and user interface screen 120 displays the resulting implanted length and the resulting implanted volume for the catheter in output box 150.

User interface screen 120 also allows a user to enter a date that IMD 12 was implanted with boxes 152. The user also may enter a location where the tip of catheter 18 of IMD 12 was implanted using drop-down menu 154, as well as a location of IMD 12 itself using drop-down menu 156. In the example of FIG. 7, the catheter tip location is indicated as "Thoracic 11," and the pump implant location is indicated as "right abdomen." A subsequent user of programmer 20 may therefore determine the location of IMD 12, e.g., to refill reservoir 30 of IMD 12 with fluid. The user also enters the orientation of the access port, e.g., 12 o'clock in the example of FIG. 7, using drop-down menu 158. The orientation of the access port assists a user in determining the location and orientation of refill port 26 of IMD 12. Various pump information such as pump model, serial number, reservoir size, calibration constant and elective replacement indicator (ERI) may be presented on the screen of FIG. 7.

Figure 8:
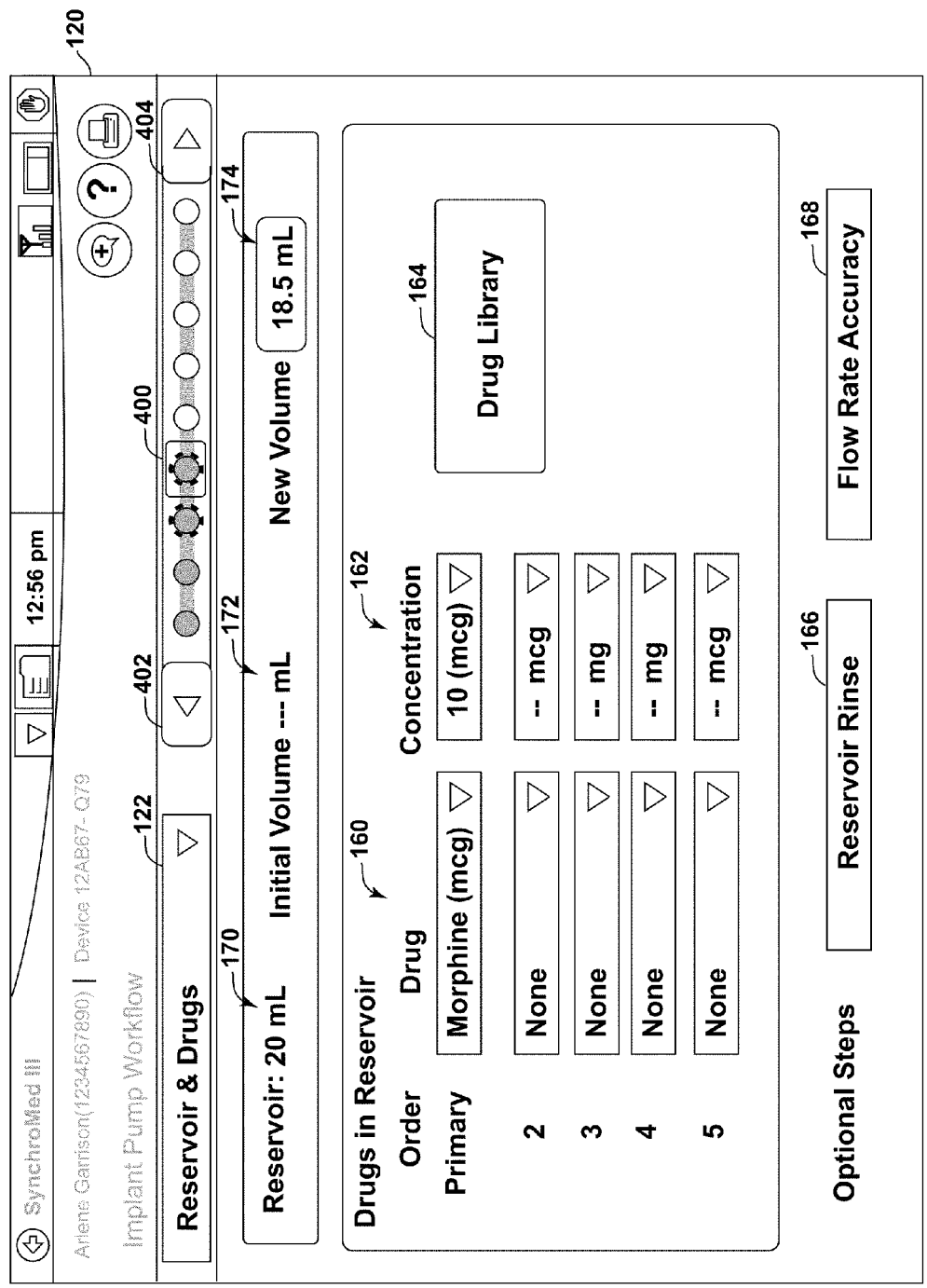
FIG. 8 is a screenshot illustrating an example user interface screen presented by an external programmer for editing drug information regarding a drug delivered by an implantable medical device.

FIG. 8 is a screenshot illustrating an example user interface screen 120 for editing therapy program information including drug information regarding a drug delivered by IMD 12. User interface screen 120 enables a user to modify drug information for drugs delivered by IMD 12. Therefore, when a subsequent user interrogates IMD 12, the subsequent user may determine the information regarding the drug delivered by IMD 12.

User interface screen 120 depicts reservoir information that indicates a maximum volume 170 of reservoir 30 of IMD 12, a starting or initial volume 172 of drug within reservoir 30 as of the time of the programming session, and a new volume 174 that will be inserted into reservoir 30 after the programming session has been completed. In one example, IMD 12, programmer 20, or both, determine initial volume 172 at the beginning of a programming session by subtracting the dispensed volume of drug delivered to patient 16 since the last programming session from the new volume 174 entered at the time of the last programming session. The dispensed volume can be determined by multiplying the rate of drug delivery (volume/time) by the amount of elapsed time drug was dispensed at that rate.

The user may also enter drug information into drug selection area 160 and concentration selection area 162. The user may select a drug from a drop-down menu of drug selection area 160 that is to be delivered to reservoir 30 of IMD 12. The user may also select a corresponding concentration of the drug from a corresponding drop-down menu of concentration selection area 162. Example drugs that may be listed by drop-down menus of drug selection area 160 include saline (as a default filler or as a placebo during clinical testing or other drug trails), morphine, bupivacaine, clonidine, hydromorphone, baclofen, alpha adrenergic agonists, baclofen, fentanyl, sufentanil, ziconotide, or other drugs or fluids. Selecting drugs from multiple drop-down menus of drug selection area 160 indicates that a combination of drugs is to be delivered to reservoir 30. For example, a user may select "morphine" from a first drop-down menu and "bupivacaine" from a second drop-down menu of drug selection area 160. When IMD 12 has already been programmed according to a dosing program with a first fluid, i.e., a fluid containing a drug at a particular concentration, user interface screen 120 displays the first drug and the first concentration of the drug. If the user changes the drug, e.g., as discussed with respect to the example of FIG. 15, processor 84 may recognize the fact that the drug and/or concentration has changed and may cause user interface screen 120 to suggest that a bridge be performed, e.g., as discussed with respect to FIG. 16.

The user may also select Drug Library 164 to link to a drug library. User interface screen 120 may then display a list of drugs and information regarding each of the listed drugs, such as names of the drugs, one or more common concentration values, and units for the concentration values. In one example, the user may select a drug from the drug library, including a concentration of the drug, and user interface screen 120 populates one or more of drop-down menus 160 and/or 162 with the user's selection. In one example, the drug library may be user definable, allowing a user to enter names of drugs, one or more concentrations that are used for the drugs, and units for the concentrations. The user may perform optional steps during the programming session, such as performing a reservoir rinse to rinse reservoir 30 of IMD 12 by selecting reservoir rinse button 166 or determining flow rate accuracy of IMD 12 by selecting flow rate accuracy button 168.

Figure 9:
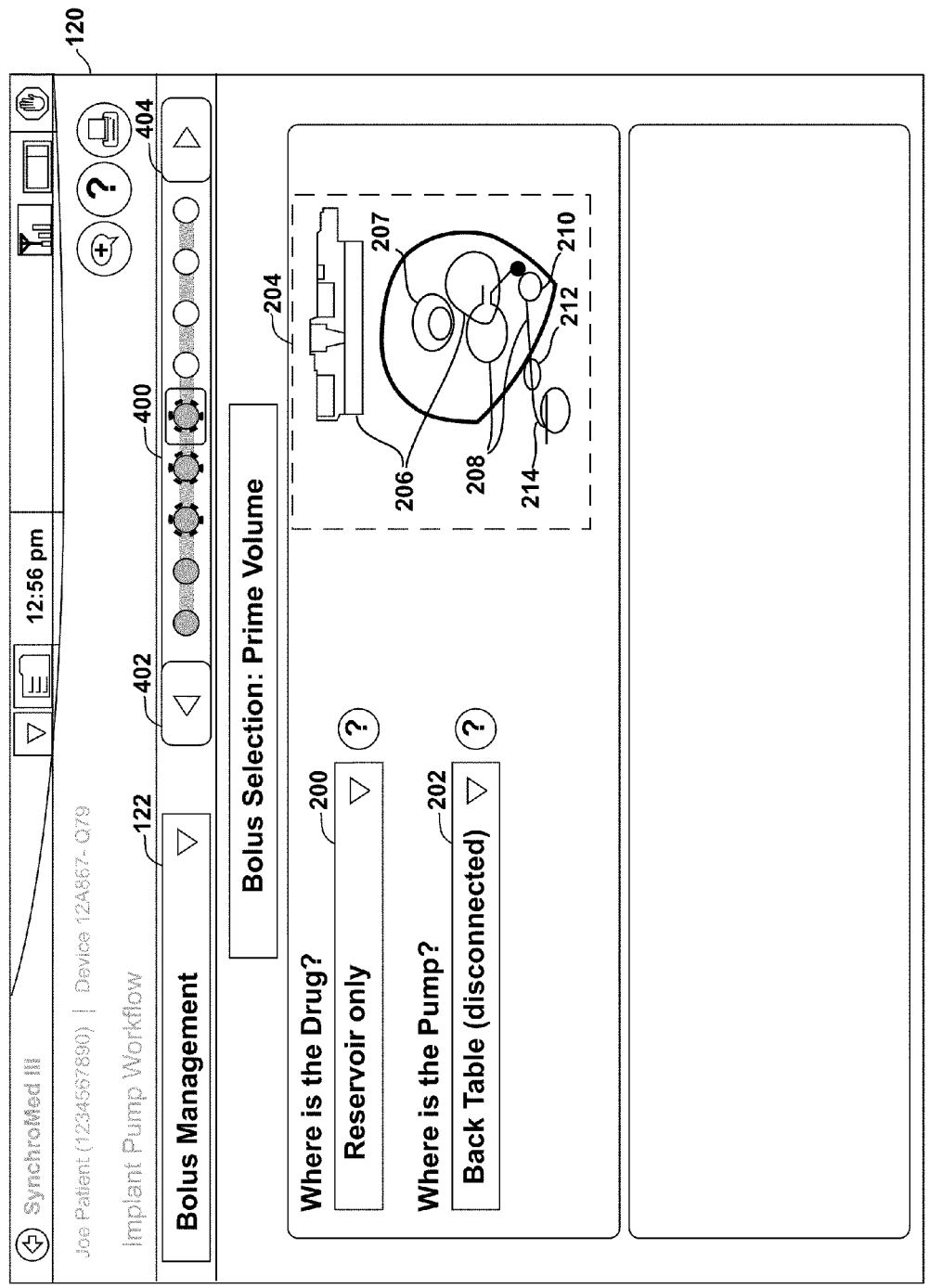
FIG. 9 is a screenshot illustrating an example user interface screen presented by an external programmer for entering drug and pump locations.

FIG. 9 is a screenshot illustrating an example user interface screen 120 for entering drug and pump locations. The example interface of FIG. 9 may be displayed by programmer 20 when a user selects "bolus management" from drop-down menu 122.

User interface screen 120 presents drug location drop-down menu 200 and pump location drop-down menu 202. A user may indicate a location of a drug within IMD 12 to programmer 20 via drop-down menu 200. Potential drug locations that may be selected from drop-down menu 200 include "Reservoir Only," "Reservoir and Tube," "Catheter Only," "Reservoir, Tube, and Catheter," "Reservoir and Catheter," and "Unknown." In this example, "Reservoir," "Tube," and "Catheter" refer to the drug pump reservoir, internal tubing and external catheter as possible locations of the drug. If the pump has not yet filled the internal tubing, for example, the location of the drug may be "Reservoir Only." The indication "Reservoir and Tube" indicates that the drug has filled the internal tubing at least partially, in addition to the presence of the drug within the reservoir. The user may also indicate a location of IMD 12 to programmer 20 via drop-down menu 202. Potential pump locations that may be selected from drop-down menu 202 include "Back Table (disconnected)" and "In Patient (connected)," which indicate that the IMD 12 (e.g., pump) is (a) on a surgical preparation table, sometimes referred to as a "back table," outside of the patient and (b) implanted within the patient and connected to the catheter, respectively.

User interface screen 120 also presents a graphical representation 204 of IMD 12. In some cases, graphical representation may include a pictorial representation. Graphical representation 204 need not include representations of all of the features of IMD 12, and may include a portion of IMD 12, e.g., one or more portions of IMD 12 at which a fluid may be present. For example, graphical representation 204 may include reservoir illustration 206, which is a pictorial representation of reservoir 30 of IMD 12, refill port illustration 207, which is a pictorial representation of refill port 26, internal tubing illustration 208, which is a pictorial representation of internal tubing 32 of IMD 12, pump illustration 210, which is a pictorial representation of fluid delivery pump 76, catheter access port illustration 212, which is a pictorial representation of catheter access port 36 of IMD 12, and catheter illustration 214, which is a pictorial representation of catheter 18 of IMD 12.

In other examples, user interface screen 120 may depict a different graphical representation 204 than the example of FIG. 9, e.g., to depict an IMD that includes additional or different components than the example of IMD 12. For example, when the IMD implanted within patient 16 includes a single long, continuous tube in place of a reservoir, such as reservoir 30, user interface screen 120 may present an illustration of an IMD that includes a single, continuous tube, rather than reservoir illustration 206. As another example, when the IMD includes a plurality of catheter segments, user interface screen 120 may illustrate each of the plurality of catheter segments with pictorial representation 204. In addition, a graphical representation of IMD 12, in various examples, may range from a precise illustration of the structure of the IMD in some cases to a rough approximation or facsimile of the structure of the IMD in other cases. In either case, the graphical illustration provides an indication of the position of the drug relative to one or more structural elements of the IMD.

Figure 10:
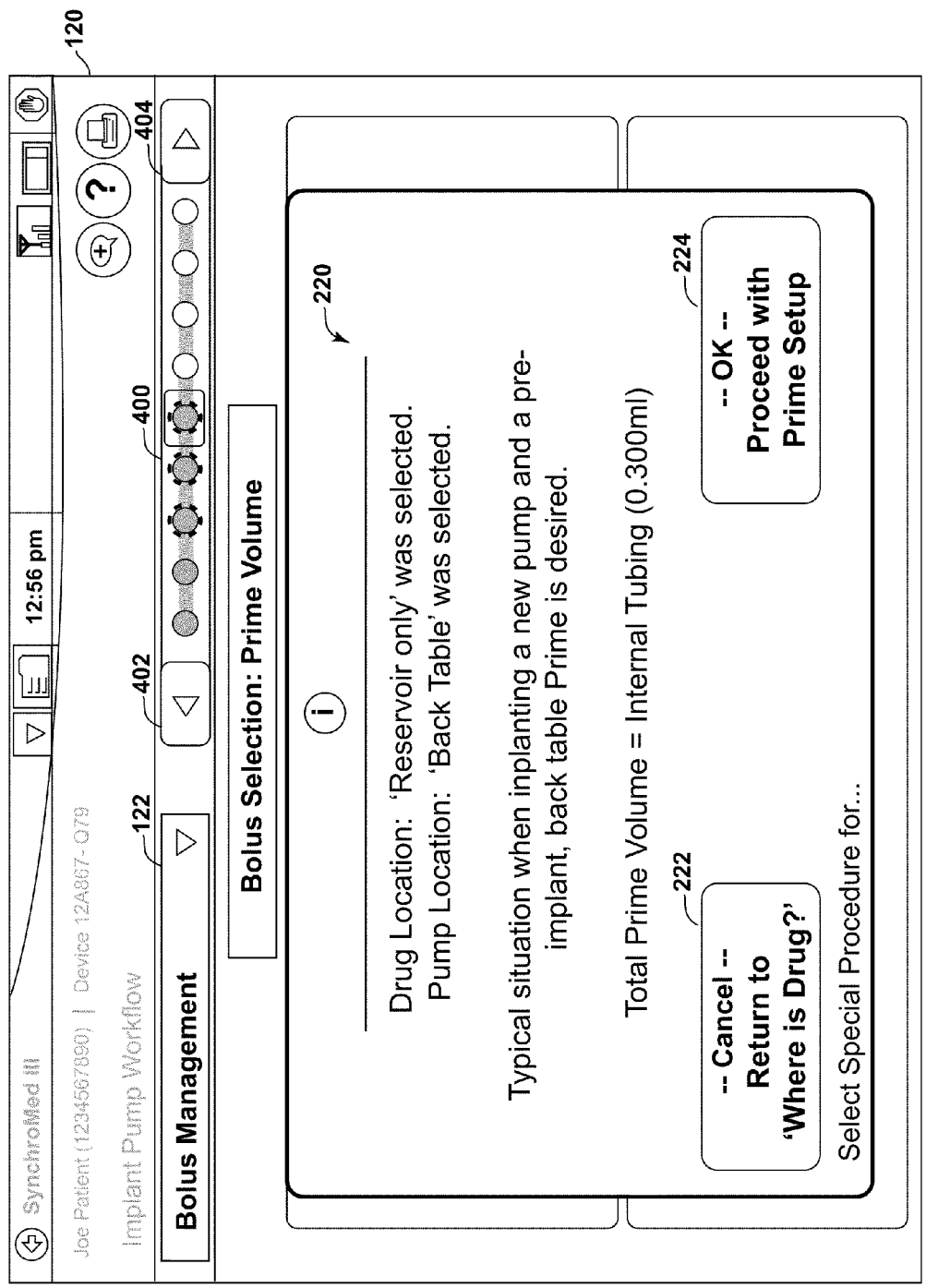
FIG. 10 is a screenshot illustrating an example user interface screen presented by an external programmer that provides a priming recommendation.

FIG. 10 is a screenshot illustrating an example user interface that provides a priming recommendation. After the user has selected an option from each of drop-down menu 200 and drop-down menu 202 (FIG. 9), user interface screen 120 updates to provide a priming recommendation, e.g., priming recommendation 220, as shown in FIG. 10. The priming recommendation is based on the selections made in drop-down menus 200, 202, i.e., the location of the drug within IMD 12 and the location of IMD 12. In the example of FIG. 10, priming recommendation 220 includes a recommendation based on the drug being in reservoir 30 of IMD 12, and IMD 12 being on the back table (thus not implanted within patient 16), where the recommendation is that the pump be primed before being implanted. The priming volume of priming recommendation 220 is based on the determined value for the volume of the internal tubing and the previously entered volume of catheter 18, when catheter 18 is connected to IMD 12. In one example, the determination of the value for the volume of the internal tubing may be based on whether IMD 12 is implanted in patient 16. In this manner, the value used for the volume of the internal tubing may assist a user in programming IMD 12 to avoid delivering a greater volume of fluid during, e.g., a priming phase, than is needed to move fluid to the tip of catheter 18.

The priming volume calculated by programmer 20 may account for expansion and contraction of the internal tubing due to heat, e.g., heat absorbed from patient 16 when IMD 12 is implanted, vis-à-vis room temperature heat when IMD 12 is not implanted and on the back table. Programmer 20 may be configured with the volume of the internal tubing both for when IMD 12 is implanted and when IMD 12 is not implanted. For example, programmer 20 may be configured such that programmer 20 uses a value for a priming volume of 0.300 mL for the internal tubing of IMD 12 when IMD 12 is implanted and a volume of 0.199 mL for the internal tubing of IMD 12 when IMD 12 is not implanted, e.g., due to temperature differences as described above. In this manner, programmer 20 may avoid programming IMD 12 to deliver fluid to patient 16 too quickly, e.g., to avoid an excessive volume of fluid for the priming volume.

Programmer 20 may calculate the priming volume for priming recommendation 220 based on whether or not catheter 18 is connected to IMD 12. When IMD 12 is implanted within patient 16, and thus catheter 18 is connected to IMD 12, programmer 20 determines that the priming volume is equal to the volume of catheter 18 plus the volume of the internal tubing. Programmer 20 calculates the volume of catheter 18 according to the radius (r) of the catheter and the length (h) of the catheter, which programmer 20 receives from the user or determines partially from known catheter characteristics, and calculates according to the formula for volume of a cylinder: $V=\pi*r^2*h$. For example, the diameter may be known for a particular type or model of catheter. However, the length will depend on the length of the catheter upon implantation, taking into account any segment that may have been removed to provide a proper implant length. Upon obtaining the catheter length, in the example of FIG. 10, when IMD 12 is implanted within patient 16, programmer 20 determines that the volume of the priming bolus necessary to move the drug to the distal tip of the catheter via the reservoir, internal tubing, and catheter is 0.300 mL+$\pi$*$r^2$*h.

When IMD 12 is on the back table and not implanted within patient 16, catheter 18 is generally not connected to IMD 12. IMD 12 therefore may determine in this case that the priming volume for the priming bolus is equal to the volume of the internal tubing only. Accordingly, programmer 20 determines that the volume of the priming bolus necessary to move fluid to the distal outlet of the internal tubing is 0.199 mL.

Priming recommendation 220 is meant only as an example of a priming recommendation based on user input. Other priming recommendations may be presented based on other inputs. For example, priming recommendations based on other example inputs may include any of a variety of recommendations, such as the recommendations depicted in Table 1:

TABLE 1

| PRIMING RECOMMENDATIONS | Where is the Pump? | |
| --- | --- | --- |
| Where is the Drug? | Back Table (Disconnected) | In Patient (Connected) |
| Reservoir Only | Prime Tube (pre-implant prime) | Prime tube & catheter |
| Reservoir and Tube | Connect Pump and Prime | Prime catheter (implant or catheter revision) |
| Catheter Only | Fill reservoir, prime internal tubing, and connect pump -OR- Fill reservoir, aspirate catheter, connect pump, prime tube and catheter with drug in reservoir | DO NOT PRIME |
| Tube and Catheter | DO NOT PRIME | DO NOT PRIME |
| Reservoir and Catheter | Prime internal tubing (pre-implant prime) | DO NOT PRIME; aspirate catheter, prime catheter and internal tubing |
| Unknown | DO NOT PRIME | DO NOT PRIME |

The example recommendations of Table 1 include recommendations for when the drug is contained in only reservoir 30, reservoir 30 and internal tubing 32, only catheter 18, internal tubing 32 and catheter 18, reservoir 30 and catheter 18, and unknown, and when IMD 12 is either disconnected from patient 16, i.e., on the back table, or connected within patient 16. In general, when IMD 12 is implanted within patient 16, catheter 18 will be connected to IMD 12, whereas when IMD 12 is not implanted, catheter 18 will not be connected to IMD 12. Therefore, when the drug is located only within reservoir 30 and when IMD 12 is not implanted, a user may prime internal tubing 32 of IMD 12 as a pre-implant prime, and another priming phase may be required once IMD 12 is implanted in patient 16 to move the drug to the tip of catheter 18.

When drug is only located within catheter 18, e.g., when IMD 12 is replaced with a new IMD or when IMD 12 is flushed, and when IMD 12 is not implanted, a user may perform one of two actions. If the drug in catheter 18 is the same as that to be inserted into reservoir 30 of IMD 12, the user may prime internal tubing 32 of IMD 12 after the drug is inserted into reservoir 30, connect IMD 12 to catheter 18, and then program IMD 12 to deliver fluid according to a dosing program. If the drug in catheter 18 is different than that to be inserted into reservoir 30, the user may aspirate catheter 18, insert the drug into reservoir 30, prime internal tubing 32, implant IMD 12, connect catheter 18, and prime catheter 18. When the drug is located in internal tubing 32 and catheter 18, no priming is necessary and the drug may simply be inserted into reservoir 30.

Programmer 20 may generally provide a recommendation of "DO NOT PRIME" when there is a risk of overdose for patient 16. For example, when fluid containing a drug is already in catheter 18 and catheter 18 is implanted within patient 16, there is a risk of overdosing patient 16 because the entire contents of catheter 18 may be delivered to patient 16 during priming. When the location of the drug is unknown, there is a risk of either overdosing patient 16, when IMD 12 is implanted, or wasting the drug, when IMD 12 is not implanted.

User interface screen 120 also presents two options to the user for priming recommendation 220, i.e., Cancel button 222 and OK button 224. When the user selects Cancel button 222, user interface screen 120 presents the screen shown in FIG. 9 so that the user can select a different drug location and/or a different pump location for IMD 12. When the user selects OK button 224, user interface screen 120 refreshes to show the screen illustrated in FIG. 11.

Figure 11:
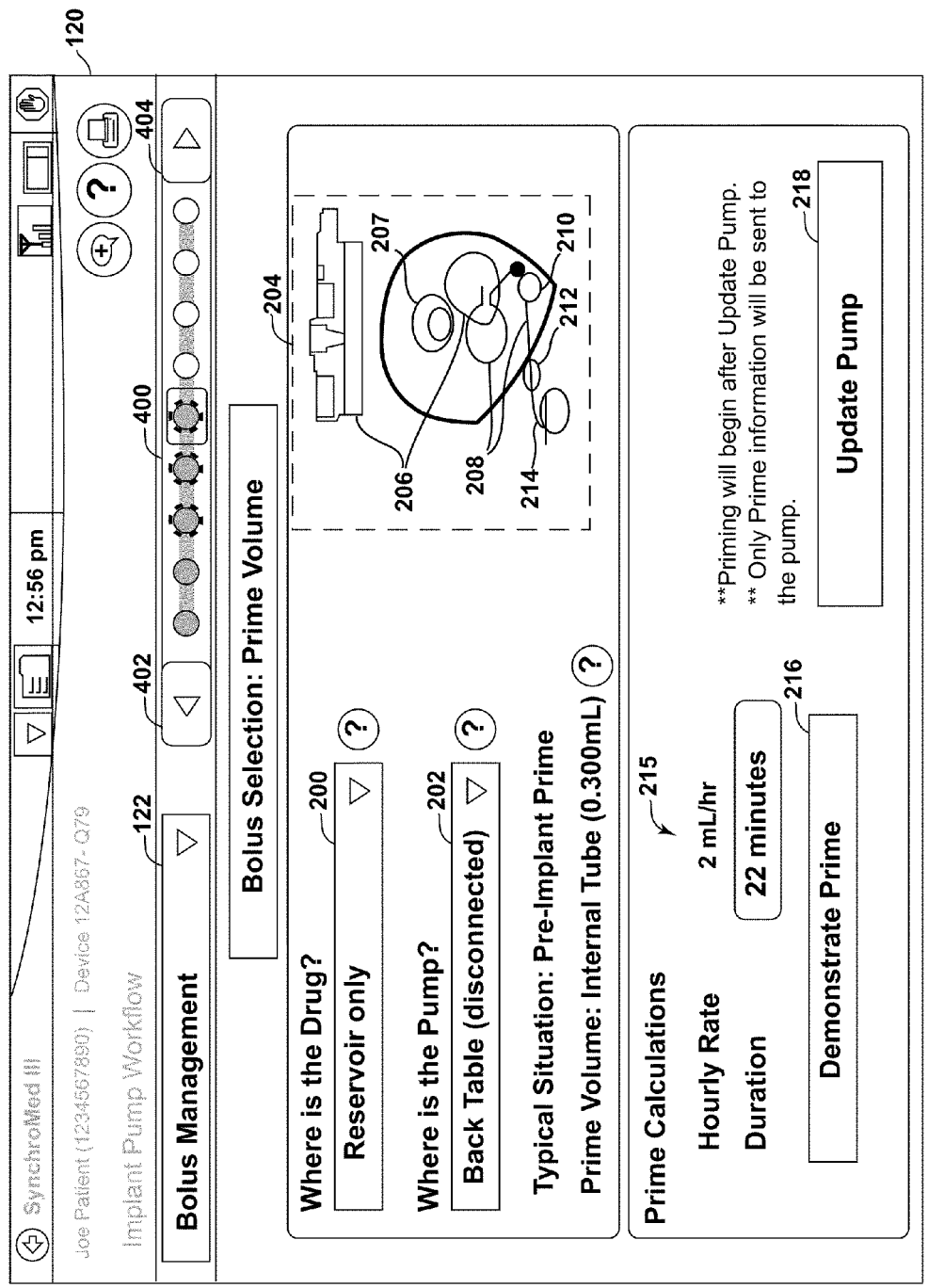
FIG. 11 is a screenshot illustrating an example user interface screen presented by an external programmer for setting up a priming phase of an implantable medical device.

FIG. 11 is a screenshot illustrating an example user interface for setting up a priming phase of IMD 12. User interface screen 120 presents prime calculations 215 that satisfy the priming requirements of IMD 12. In the example depicted in FIG. 11, prime calculations 215 include an hourly rate of 2 mL/hr and a duration of 22 minutes. These calculations are based on the concentration of drug in reservoir 30 of IMD 12 (as received by programmer 20 with the screen of FIG. 8), the location of the drug, the length of the internal tubing of IMD 12, and the length of catheter 18. The user may modify the setup of the priming phase by changing the duration or priming volume of user interface screen 120. In general, the priming phase may drive IMD 12 at the fastest possible rate to move fluid to the tip of catheter 18 as quickly as possible. However, if desired, the user may adjust the priming phase by modifying the duration of the priming phase, by modifying the priming rate, or by modifying the priming volume. The user may also select Demonstrate Prime button 216 or Update Pump button 218. When the user selects Demonstrate Prime button 216, user interface screen 120 presents a representation of the priming phase of IMD 12, such as discussed with respect to the examples of FIGS. 12A-12C. When the user selects Update Pump button 218, programmer 20 sends a signal to IMD 12 to update programming of IMD 12 via telemetry module 88, e.g., as discussed with respect to the examples of FIG. 13 and FIG. 14.

Figure 12A:
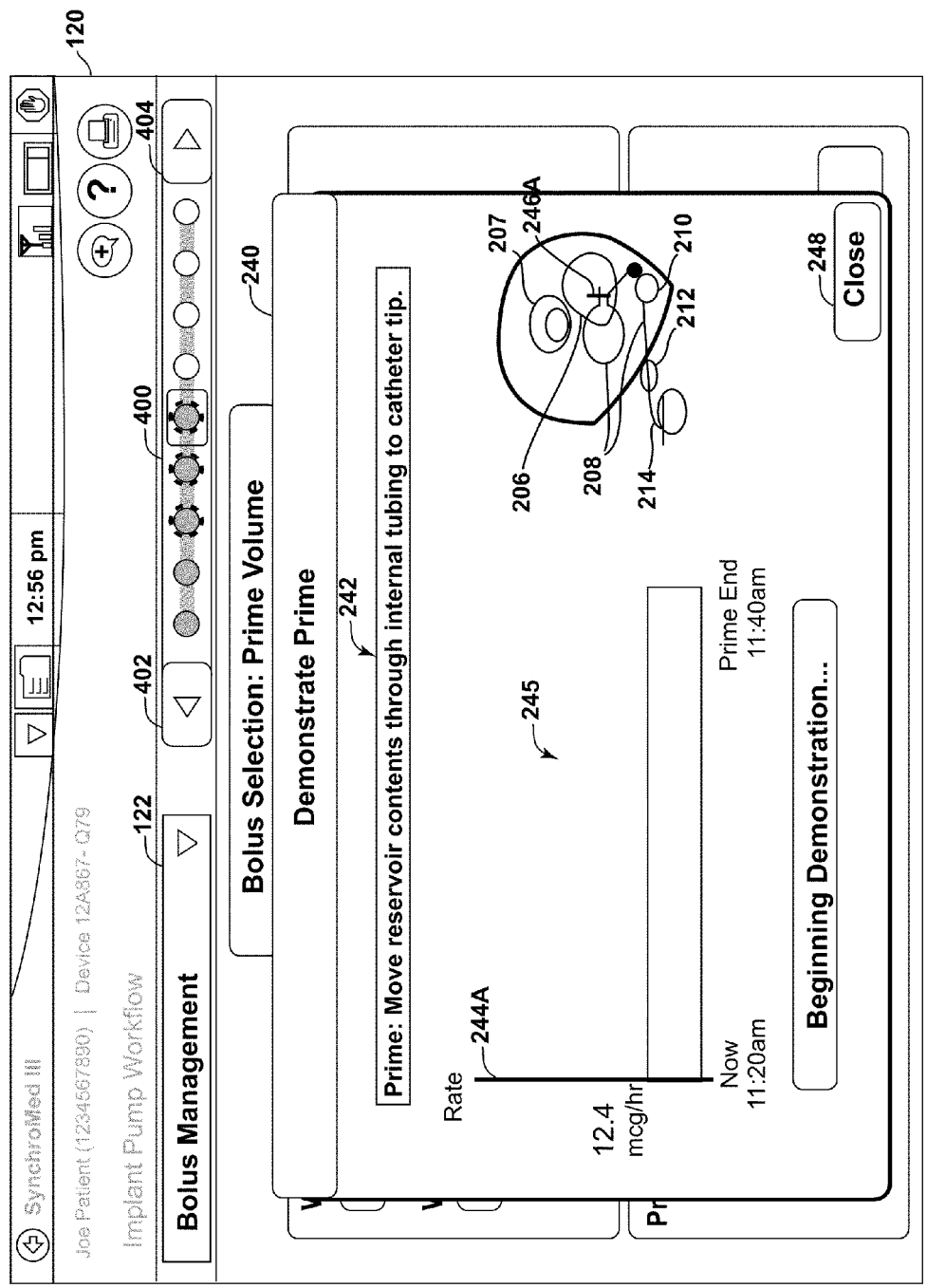
FIGS. 12A-12C are screenshots illustrating an example of a user interface screen presented by an external programmer that presents a representation of progress of a priming phase of an implantable medical device and that displays an indication of a location of a fluid within the implantable medical device.
Figure 12B:
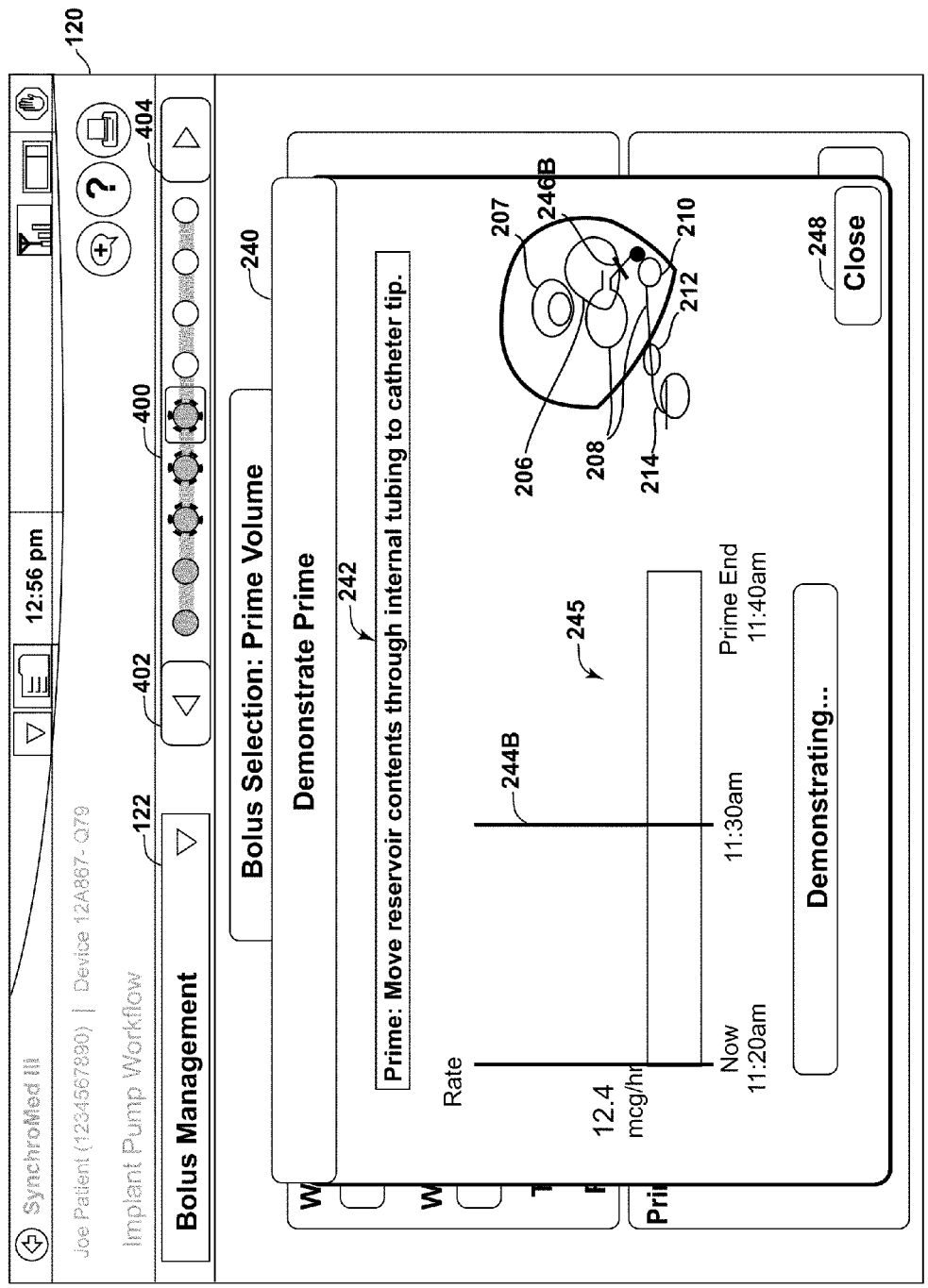
Figure 12C:
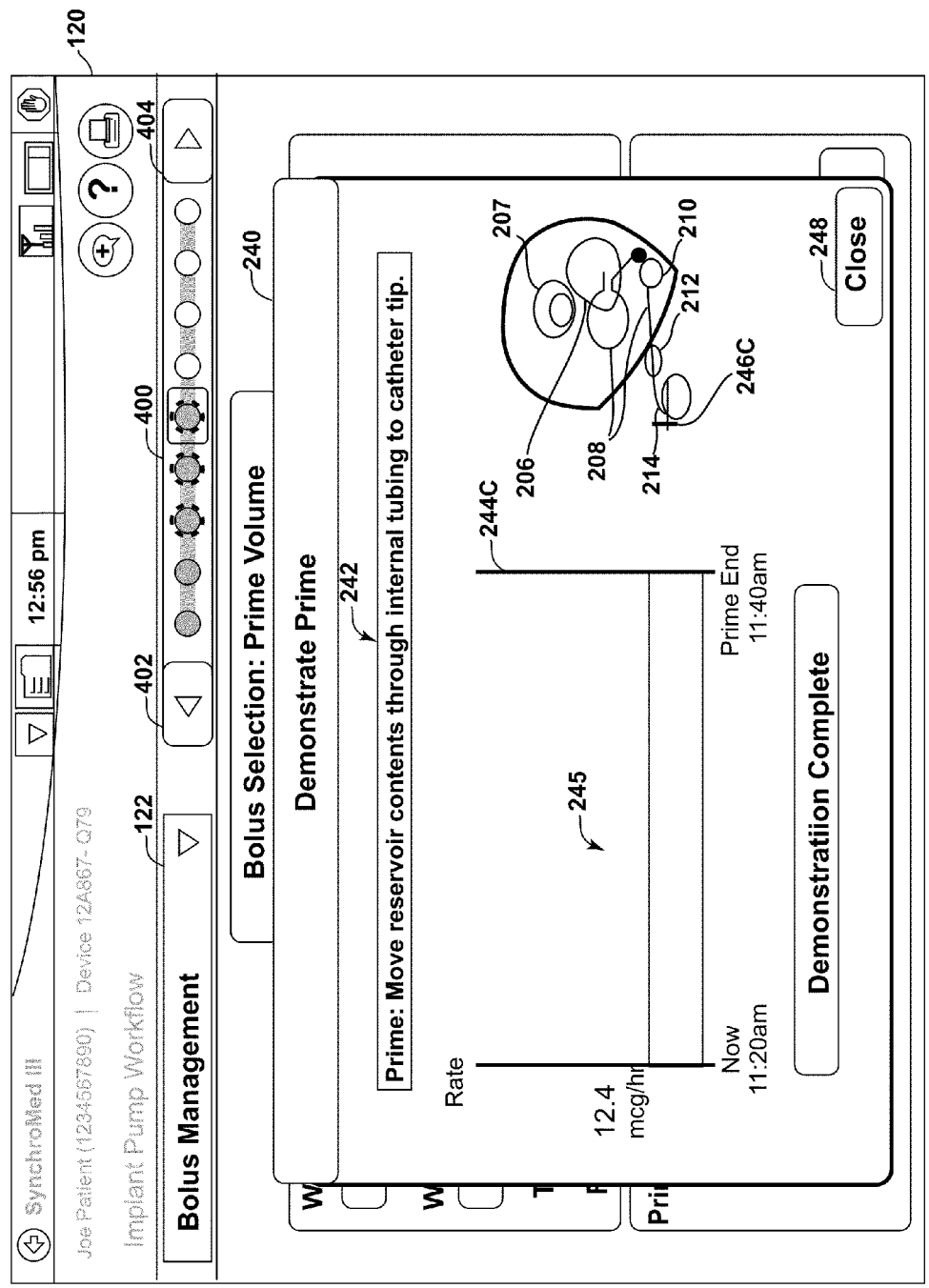

FIGS. 12A-12C are example screenshots illustrating a window 240 that presents a representation of progress 244 of a priming phase of IMD 12. Window 240 of the examples of FIGS. 12A-12C also displays an indication 246 of a location of fluid within IMD 12 during the priming phase. In particular, indication 246 may indicate a distal-most position of the fluid within the internal tubing and catheter, assuming that the connection point of the internal tubing is considered most proximal and the end of the catheter opposite the end that connects to the pump is considered most distal. In other words, indication 246 may indicate a fill level of the fluid along the length of the tubing and catheter. User interface screen 120 may display window 240 when the user selects Demonstrate Prime button 216. User interface screen 120 then displays window 240 as a simulation of the priming phase of IMD 12. User interface screen 120 may also display a window similar to window 240 during the actual priming phase of IMD 12. Programmer 20 may display a similar window to simulate a bridging phase of IMD 12 or during an actual bridging phase of IMD 12. In one example, programmer 20 may further depict a representation of a supplemental bolus, such as a one-time therapeutic bolus, that may occur during a therapy schedule of a dosing program or following the priming phase of IMD 12.

Window 240 generally depicts an animation of a status bar and fluid location within the graphical representation of IMD 12. Window 240 also may provide description 242, which describes the animation of window 240, i.e., that the priming phase of IMD 12 is to "move reservoir contents through internal tubing to catheter tip." Window 240 also provides Close button 248. When the user selects Close button 248, window 240 will close and user interface screen 120 will return to the screen depicted in FIG. 11. The animation of window 240 may be substantially shorter than the actual time required for the priming phase of IMD 12. For example, the animation may last a few minutes to a few seconds, e.g., between five and ten seconds. Window 240 may include other indicators as well, such as a volume of fluid that has already been delivered, a rate at which fluid is being delivered, an amount of time remaining for the priming phase, or other indicators.

Other examples may use other means for representing a status of the priming phase of IMD 12 and the location of fluid within IMD 12. For example, window 240 may present a textual timer that counts down to zero, a textual timer that counts up to a specific time, a chart or graphical box that is shaded, cross-hatched, or otherwise filled to a position representative of the percent completion of the priming phase, or other indications of a status of the priming phase of IMD 12. An example of window 240 may also represent a location of the fluid within IMD 12 with a continuous colored line that represents the fluid within IMD 12, a line style, such as a dashed line or dotted line, to represent the fluid, highlighting portions of the tubing and catheter representations that contain the fluid, using a flashing or blinking continuous line or bar that corresponds to the location of the fluid, a cross-hatched line or bar that represents the fluid, shading the representations of the internal tubing and the catheter that contain the fluid, or other means for representing a location of fluid within the graphical representation of IMD 12. Window 240 may present a continuous animation or a series of discrete steps corresponding to various locations within IMD 12 to track the location of fluid within IMD 12 during the priming phase of IMD 12.

Programmer 20 may determine a location of the fluid by various methods. In general, processor 84 executes a function, e.g., according to instructions stored in memory 86, to determine or predict a location of the fluid within IMD 12. The function may include factors that account for a rate at which IMD 12 will deliver the priming bolus, known or estimated volumes of internal tubing 32 of IMD 12, known or estimated volume of catheter 18 of IMD 12, and a timer to track the current time or a time representative of a priming phase of IMD 12. In one example, the function returns a result corresponding to a volume of internal tubing and catheter 18 that has been filled at a time t. For example, the function Delivered_Volume(time) may return a volume for the equation "rate*time". The volume returned by Delivered_Volume(time) may correspond to a volume of fluid that has been delivered. When the returned volume is less than the total volume of internal tubing 32, processor 84 determines that the fluid is still within internal tubing 32.

When the returned volume exceeds the volume of internal tubing 32, processor 84 determines that the fluid has reached catheter 18. When the returned volume is equal to the volumes of catheter 18 and internal tubing 32, processor 84 determines that the fluid has reached the tip of catheter 18. The function Location(time) may further determine a current location by dividing the volume determined by Delivered_Volume(time) by the total volumes of internal tubing 32 and/or catheter 18. For example, when the volume determined by Delivered_Volume(time) is less than the volume of internal tubing 32, Location(time) may return a percentage of internal tubing 32 that has been filled by dividing the result of Delivered_Volume(time) by the volume of internal tubing 32. When the volume determined by Delivered_Volume(time) exceeds the volume of internal tubing 32, Location(time) may return a percentage of catheter 18 that has been filled by dividing the result of Delivered_Volume(time) by the volume of catheter 18 or the sum of the volumes of the internal tubing and catheter, or subtracting the volume of the internal tubing form the Delivered_Volume(time) and dividing the result by the volume of catheter 18. In one example, processor 84 may execute functions corresponding to the following pseudocode, which may be stored in memory 86, to determine a location of fluid within IMD 12:

```
float Delivered_Volume(float time, float rate) {
    /* Returns a float value corresponding to the amount of fluid that has been delivered
     * when fluid is delivered at rate for time */
        return (rate * time);
}
float Location(float time, float rate, float catheter_volume, float tubing_volume) {
    /* Returns a float value corresponding to the current location of fluid when the fluid
     * has been delivered at rate for time */
        float delivered_volume = Delivered_Volume(time, rate);
        if (delivered_volume < tubing_volume) {
            return (delivered_volume / tubing_volume);
        }
```

```
        else {
            return ((delivered_volume – tubing volume) / (catheter_volume));
            // subtract tubing volume to determine percent fill of catheter
        }
    }
}
```

FIG. 12A illustrates window 240 at the time immediately after the user selects Demonstrate Prime button 216 (FIG. 11), i.e., at the beginning of the priming phase of IMD 12. Window 240, in the example of FIG. 12A, at this time depicts status bar 244A at the beginning of timeline 245, to indicate the beginning of the priming phase of IMD 12. In the example of FIG. 12A, window 240 also depicts fluid location 246A with a line at the intersection of the graphical representation 206 of reservoir 30 and the graphical representation 208 of internal tubing 32. In other examples, window 240 may depict the fluid location with other visual cues, such as a colored line representative of the fluid, highlighting of areas containing the fluid, cross-hatching of the area containing the fluid, a flashing line representative of the fluid location, or other indicators.

FIG. 12B illustrates window 240 at approximately the half-way point of the priming phase of IMD 12. Window 240, accordingly, depicts status bar 244B approximately half-way across timeline 245. Window 240 also depicts fluid location 246B as being near the end of the graphical representation 208 of internal tubing 32, before having reached graphical representation 210 of fluid delivery pump 46.

FIG. 12C illustrates window 204 at the end of the priming phase of IMD 12. Window 240 depicts status bar 244C at the end of timeline 245 and the fluid location 246C at the end of graphical representation 214 of catheter 18, i.e., at the distal tip, indicating that the catheter and internal tubing have been fully primed and are ready for use in delivery of the drug to a patient according to pertinent therapy program information specified for the patient. In this manner, user interface screen 120 may present a representation of progress 244 of a priming phase of IMD 12, display a representation 204 of at least a portion of IMD 12, and display an indication 246 of a location of fluid within IMD 12. The user may therefore observe the behavior of fluid throughout IMD 12 during the priming phase. In one example, window 240 displays an animation in which status bar 244 and fluid location 246 are each updated continuously. In another example, window 240 displays status bar 244 and fluid location 246 in a step-wise manner. In other examples, window 240 may display only one of either status bar 244 or fluid location 246.

In this manner, the screenshots of FIGS. 12A-12C demonstrate examples of displaying a representation of a portion of an implantable fluid delivery device via a user interface associated with a programmer device that communicates with the implantable fluid delivery device and displaying an indication of a location of fluid within the implantable fluid delivery device during a delivery phase via the user interface. The screenshots of FIGS. 12A-12C also demonstrate examples of displaying a representation of progress of the delivery phase of the implantable fluid delivery device.

Figure 13:
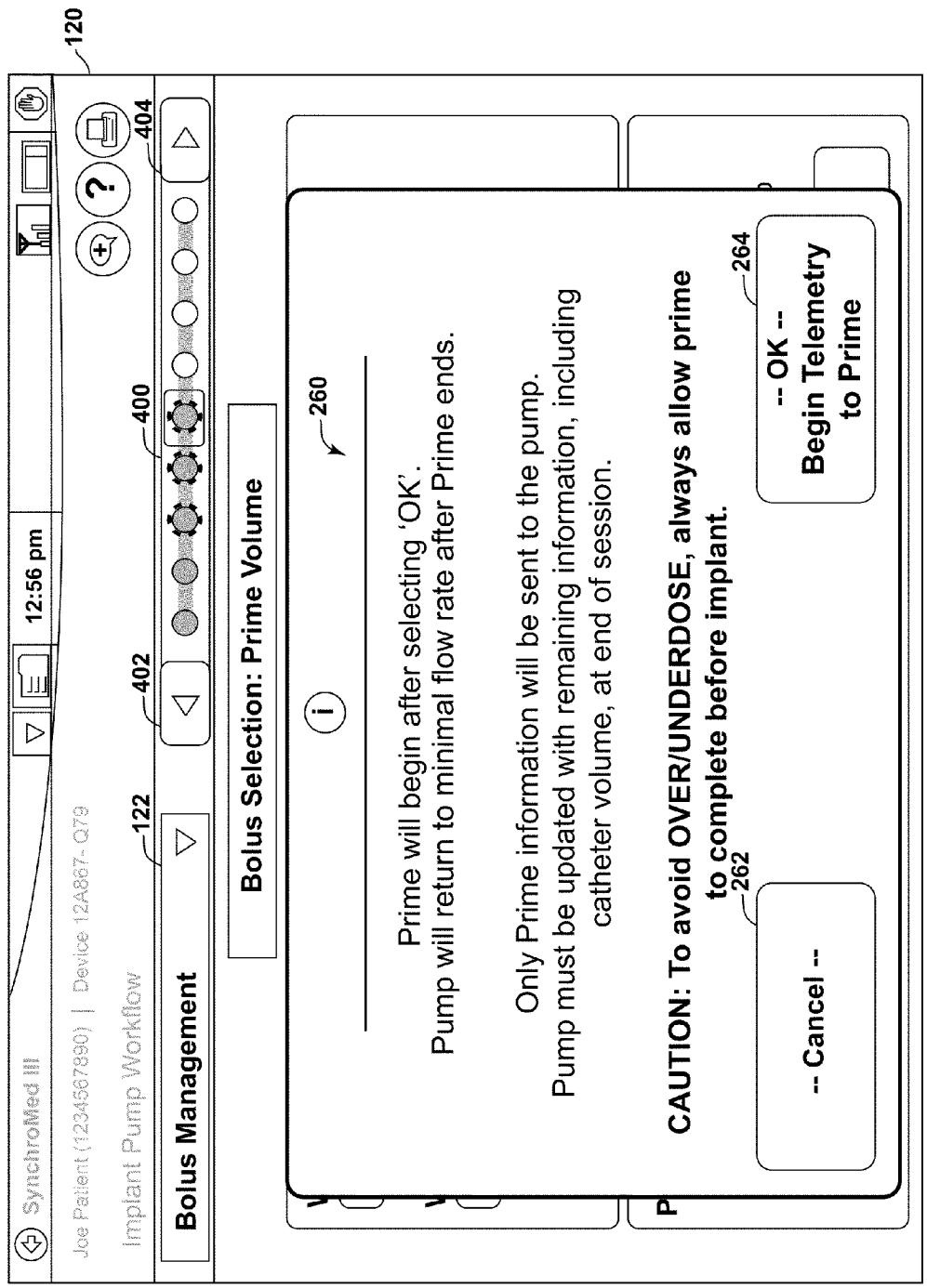
FIG. 13 is a screenshot illustrating an example user interface screen presented by an external programmer for initiating communication with an implantable medical device.

FIG. 13 is a screenshot illustrating an example user interface for initiating communication with IMD 12. That is, user interface screen 120 allows the user to initiate the priming phase of IMD 12 with the programming of IMD 12 that programmer 20 received from the screen of FIG. 11. User interface screen 120 displays the example screenshot of FIG. 13 when the user selects Update Pump button 218 (FIG. 11).

User interface screen 120 illustrates message 260 for the user, which indicates that priming will begin and that additional programming may be necessary for IMD 12. User interface screen 120 also presents Cancel button 262 and OK—Begin Telemetry to Prime button 264 ("OK button 264"). When the user selects Cancel button 262, user interface screen 120 reverts to the display illustrated in FIG. 11 and allows the user to modify the priming phase setup of IMD 12. When the user selects OK button 264, programmer 20 initiates communication with IMD 12 via telemetry module 88 to program IMD 12 and to begin the priming phase of IMD 12. User interface screen 120 also presents the screen illustrated in FIG. 14 after the user selects OK button 264.

Figure 14:
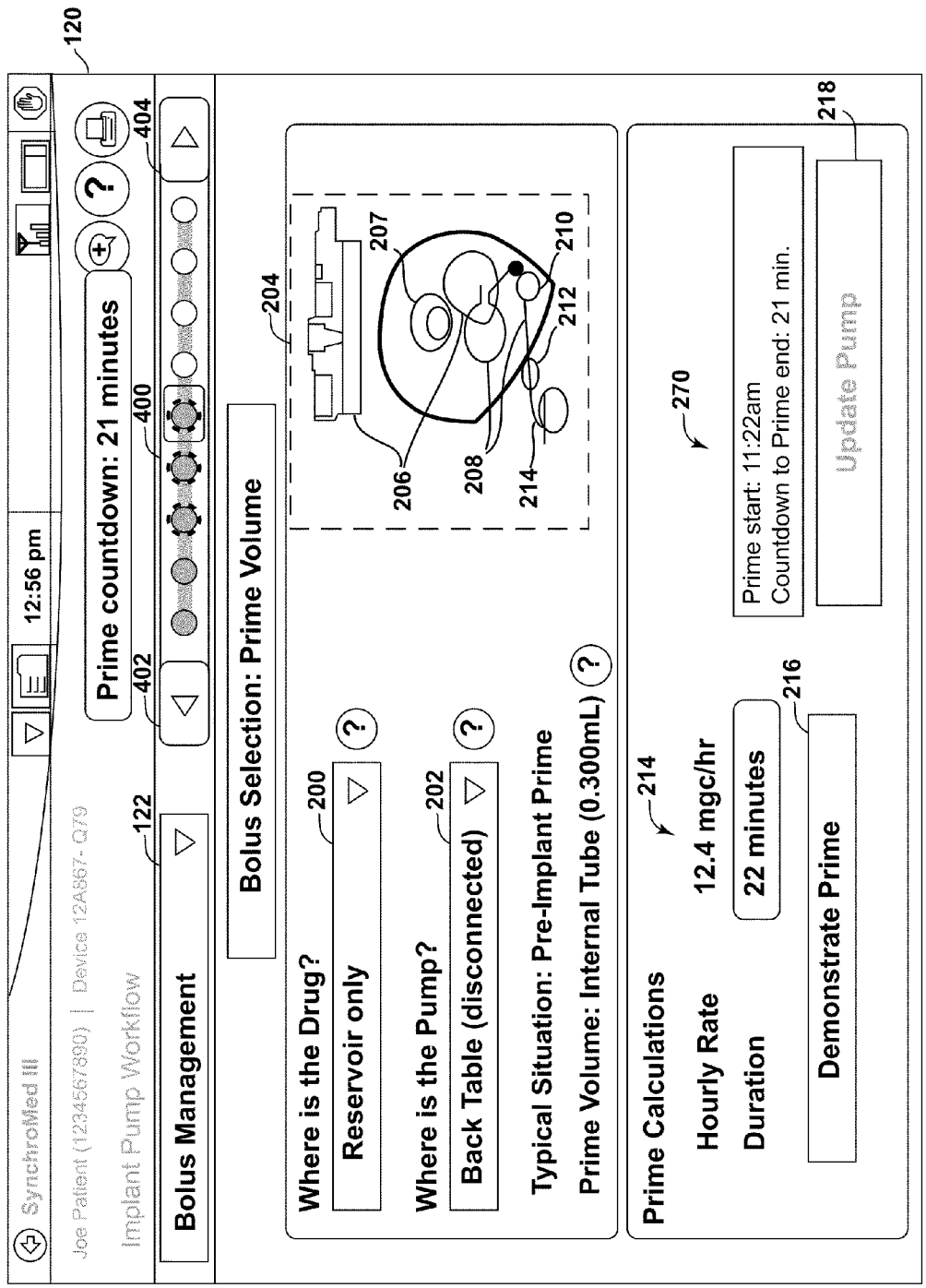
FIG. 14 is a screenshot illustrating an example user interface screen presented by an external programmer that depicts a message indicating a time at which a priming phase of an implantable medical device will be finished.

FIG. 14 is a screenshot illustrating user interface screen 120 after the user selects OK button 264 (FIG. 13). Much of the same information is presented in FIG. 14 as in FIG. 11. However, user interface screen 120 updates to depict priming message 270, which indicates a time at which the priming phase of IMD 12 began ("Prime Start") and a countdown to a time at which the priming phase of IMD 12 will be finished ("Countdown to Prime end"). In one example, when the user selects Demonstrate Prime button 216 at this point, user interface screen 120 depicts a window similar to window 240 (FIGS. 12A-12C), but depicts actual progress of the priming phase of IMD 12, as well as an indication of the current location of fluid within IMD 12.

In another example, user interface screen 120 may display a different button that allows the user to request that user interface screen 120 depict a representation of the status of the priming phase and an indication of a location of fluid when IMD 12 is actually being primed. That is, rather than demonstrating a simulation of the priming phase of IMD 12, processor 84 may calculate an estimated location of the fluid as of the current time, during the priming phase of IMD 12, and depict the estimated location of the fluid, along with the representation of the actual priming phase of IMD 12. Processor 84 of programmer 20 may estimate the actual location of fluid within IMD 12, based on the time since the user selected OK button 264, and based on calculations of the volumes of internal tubing 32 of IMD 12 and catheter 18 of IMD 12 and causes user interface screen 120 to display the estimated location of fluid in IMD 12 in the window.

User interface screen 120 also includes prime calculations 215, which may correspond to prime calculations 215 of FIG. 11. Prime calculations 215 represent the rate at which IMD 12 is delivering the priming bolus and the total time for the priming phase of IMD 12. In one example, user interface screen 120 may gray out drop-down menus 200 and 202 to prevent the user from modifying programming of a drug location and a location of IMD 12 after priming of IMD 12 has begun.

Figure 15:
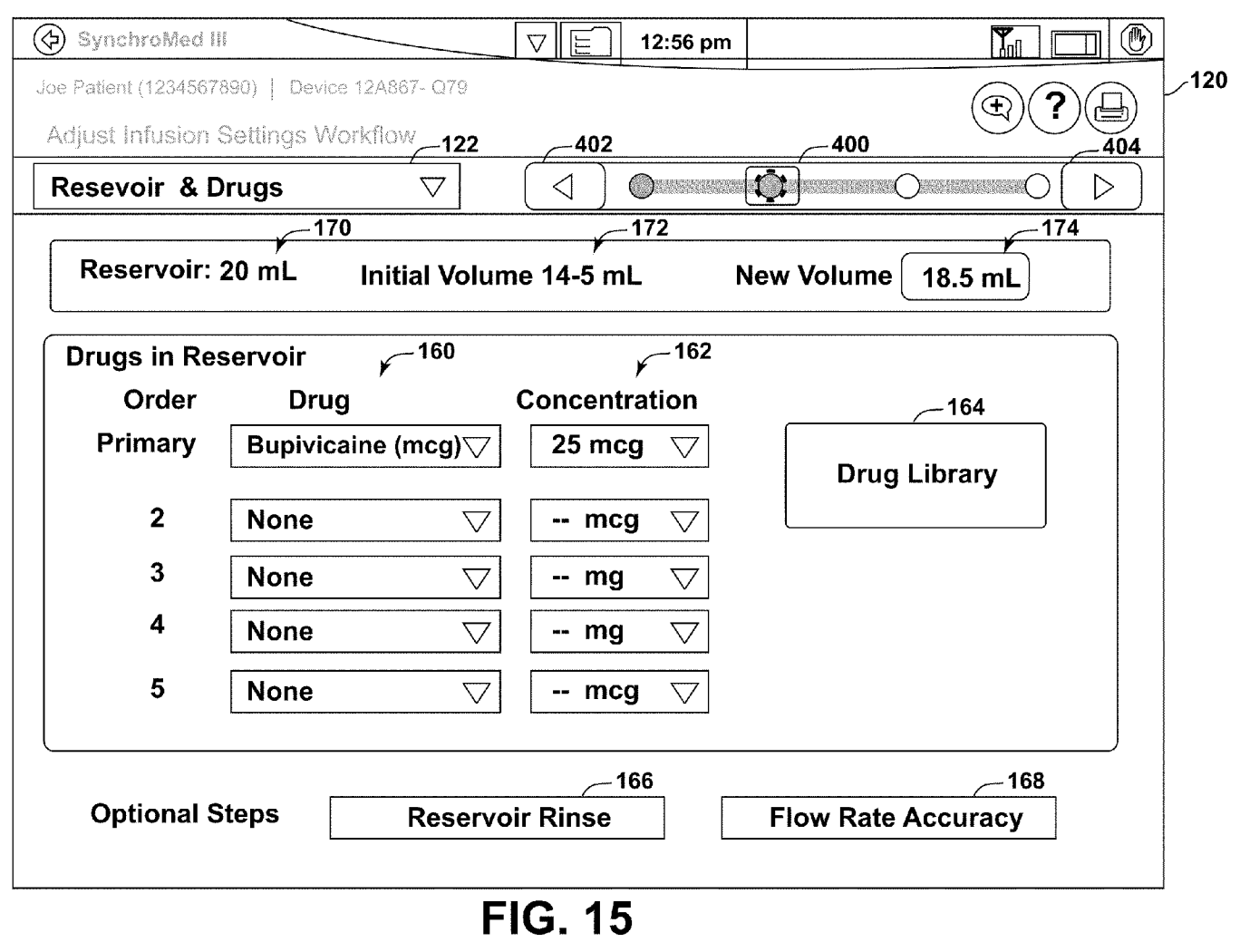

FIG. 15 is a screenshot illustrating user interface screen 120 after a user has selected "Reservoir & Drugs" from drop-down menu 122 and changed drug information 160 from "Morphine," as depicted in FIG. 8, to "Bupivicane." In general, when drug information 160 or concentration information 162 changes for a particular IMD 12, programmer 20 recommends that a bridge procedure be performed to deliver the old drug according to an original dosing program and to begin to deliver a new drug according to a new dosing program. In general, a bridge procedure is a procedure conducted when a new fluid containing a different drug or a different concentration of the same, old drug is inserted into reservoir 30 of IMD 12 while IMD 12 is in the process of delivering a different fluid, i.e., an original fluid containing an original drug at an original concentration. The bridge procedure controls IMD 12 to deliver the original fluid at a first rate or with the original dosing program until the original fluid is completely delivered, then causes IMD 12 to deliver the new fluid at a second rate or with the new dosing program. In this manner, IMD 12 may avoid delivering the original fluid according to a dosing program intended for the new fluid. Programmer 20 may further program IMD 12 to automatically switch from the original dosing program to the new dosing program when the old fluid has been completely delivered.

For example, when IMD 12 includes 10 mL of fluid containing morphine and receives a 10 mL injection of fluid that contains bupivacaine, programmer 20 may program IMD 12 to deliver fluid a first rate until 10 mL of fluid have been delivered, then to deliver fluid at a second rate. As another example, programmer 20 may program IMD 12 to deliver fluid according to a first dosing program until 10 mL of fluid have been delivered, then to deliver fluid according to a second dosing program.

Figure 16:
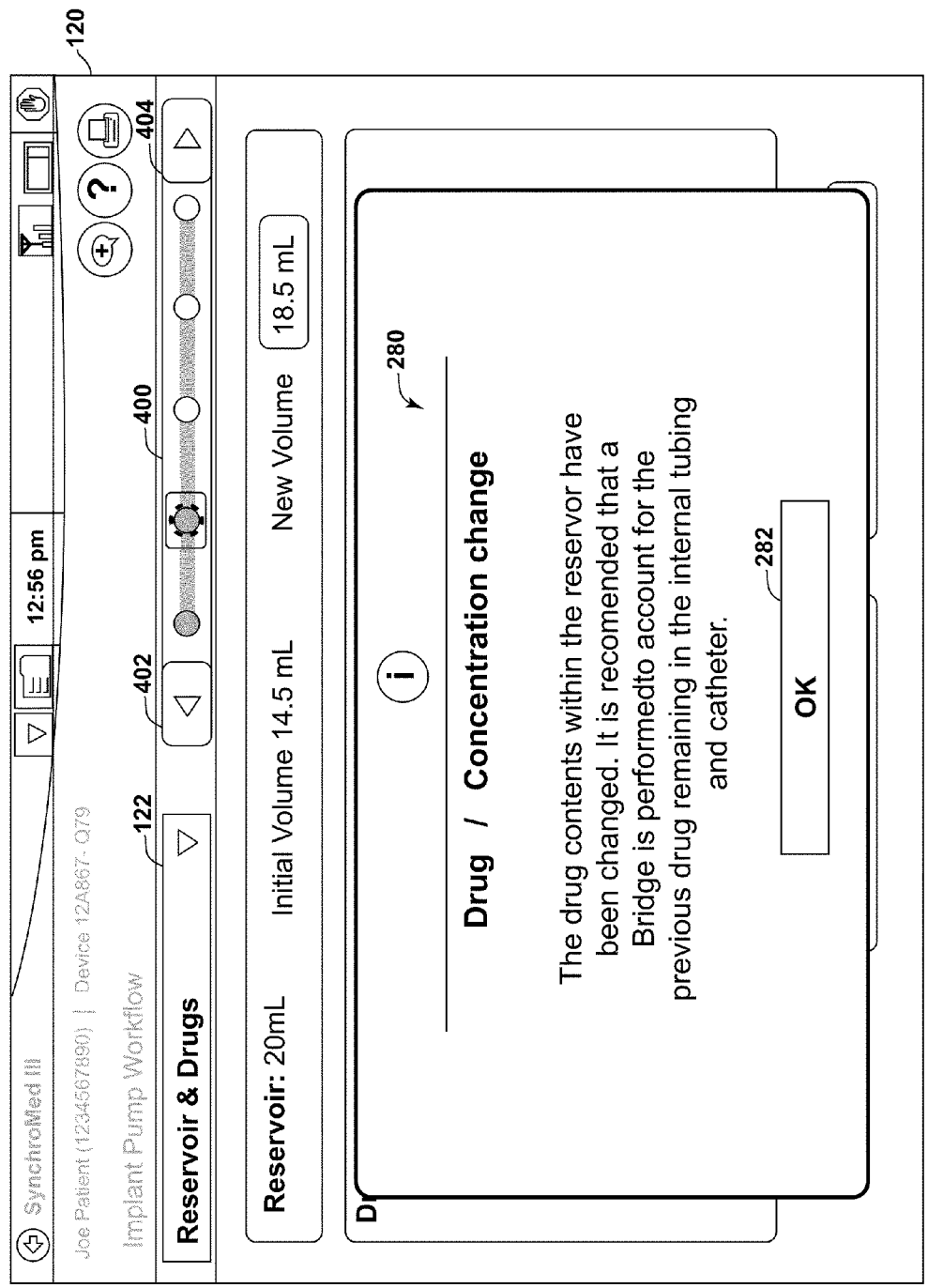
FIG. 16 is a screenshot illustrating an example user interface screen presented by an external programmer that depicts a bridging recommendation after a user has changed drug and/or concentration information.

FIG. 16 is a screenshot illustrating user interface screen 120 after the user has modified drug and/or concentration information. User interface screen 120 illustrates bridge recommendation 280 when the user changes drug and/or concentration information using drop-down menus 120, 122 (FIG. 15). Programmer 20, in the example of FIG. 16, determines that the drug and/or concentration have changed from a previous drug/fluid by comparing the input received, e.g., with the user interface of FIG. 15 to a historical program of IMD 12. When programmer 20 detects that either the drug or the concentration of the drug have changed, user interface screen 120 presents message 280 that recommends that a bridge be performed. A bridge may be necessary to prevent overdosing or underdosing of patient 16. That is, if IMD 12 were to deliver the current drug at the current concentration to patient 16 according to the programming for the new drug and/or new concentration, patient 16 may receive the old drug at a rate that is too fast or too slow for therapeutic benefit. Therefore, programmer 20 recommends that a bridge be performed to deliver the current drug at the current concentration to patient 16 at a first rate or according to a first dosing program, and then to switch to a new rate or new dosing program once all of the current drug has been delivered, in accordance with the bridge. The user may select OK button 282 to cause programmer 20 to set up and perform the bridge. Programmer 20 may present the example user interface of FIG. 17 to the user to set up and perform the bridge.

Figure 17:
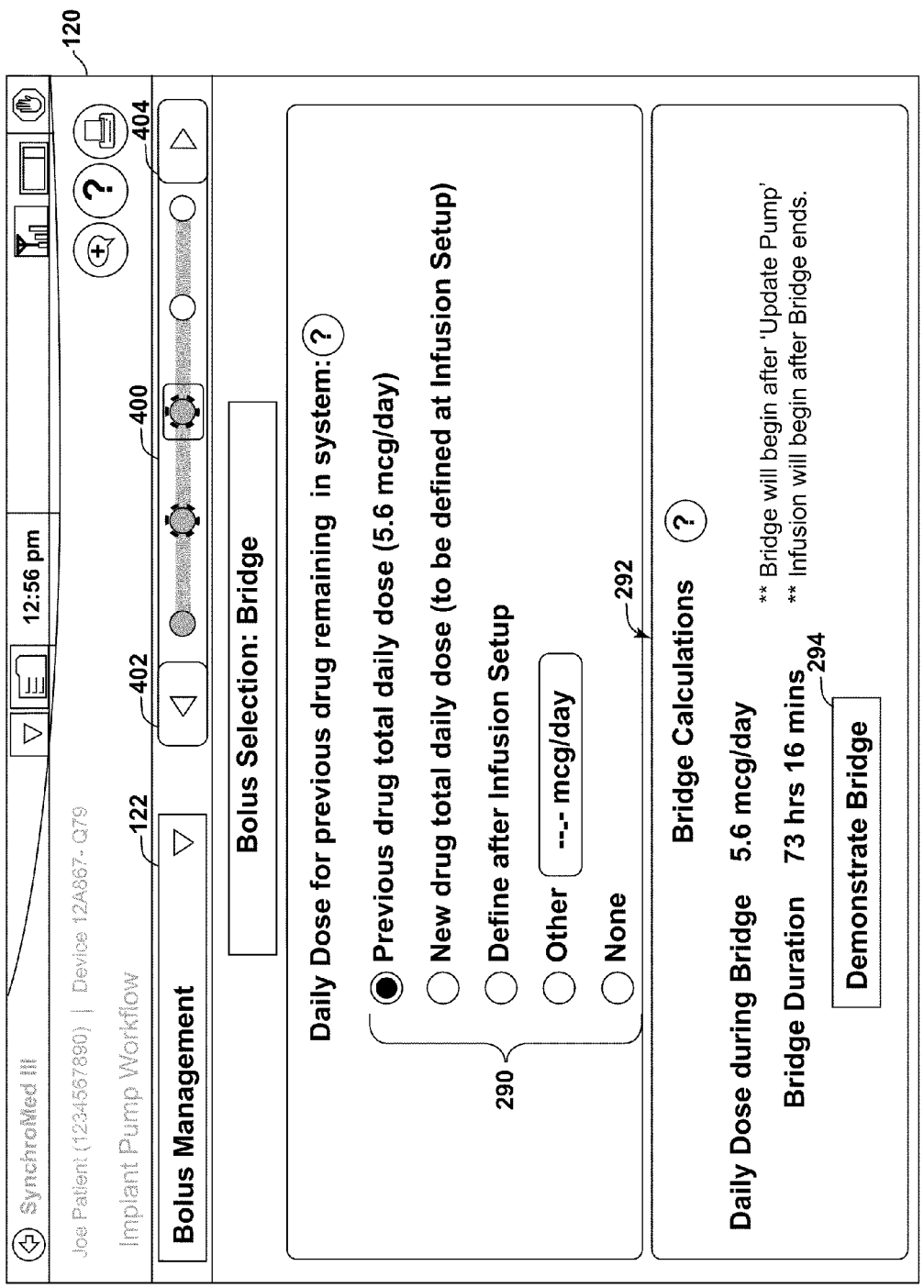
FIG. 17 is a screenshot illustrating an example user interface screen presented by an external programmer for receiving bridging information from a user.

FIG. 17 is a screenshot illustrating user interface screen 120 for receiving bridging information from the user. User interface screen 120 may display a screen similar to FIG. 17 after the user selects OK button 282 (FIG. 16) to perform a bridge. In this example, user interface screen 120 presents radio buttons 290 that enable the user to select from among various options for expending the old drug remaining in IMD 12. For example, the user may elect to 1) deliver the previous drug at the previous daily dose; 2) deliver the old drug at a new daily dose; 3) define the bridging procedure at a later time, i.e., after setting up infusion (to program the bridge later); 4) "other" to define a daily dosage in micrograms per day; or 5) none, to deliver the old drug according to the programming intended for the new drug. When the user selects "Define after Infusion Setup," programmer 20 records the fact that the bridge has not yet been established and may present another message to the user requesting that the user define the bridge when, for example, the user attempts to update IMD 12. Programmer 20 may present a user interface similar to the example of FIG. 17 after the user has modified a program for IMD 12 for the new drug when the user selects "Define after Infusion Setup."

Based on the user's selection from radio buttons 290, programmer 20 calculates elements of the bridge procedure and displays bridge calculations 292. In the example of FIG. 17, bridge calculations include a daily dose of 5.6 mcg/day of the old drug. Bridge calculations 292 also include an indication that the bridge will last for 73 hours and 16 minutes at the current rate of delivery. That is, IMD 12 will continue to deliver the old drug at a rate of 5.6 mcg/day for 73 hours and 16 minutes, if the user elects to program IMD 12 with this configuration. After the bridge has finished, IMD 12 will switch to a dosing program corresponding to a new drug or new concentration. For example, IMD 12 may be programmed to deliver a first quantity of fluid according to bridge calculations 292, or according to a first dosing program, and then switch to a second dosing program after the first quantity of fluid has been delivered. The user may then elect to use this configuration, change the configuration, or select Demonstrate Bridge button 294, which presents a window similar to window 294 (FIGS. 12A-12C) to demonstrate the bridge procedure.

Figure 18A:
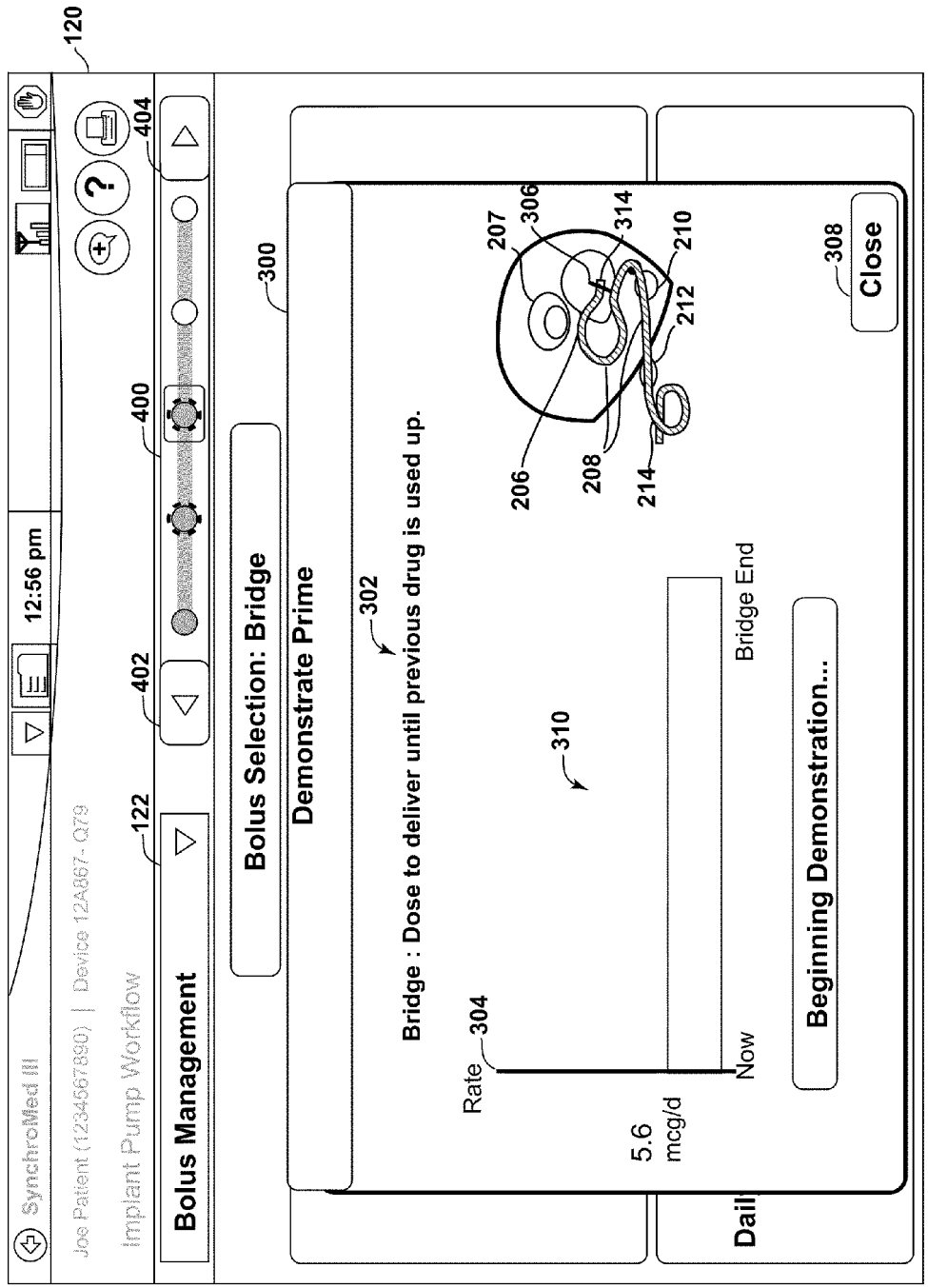
FIGS. 18A and 18B are screenshots illustrating an example user interface screen presented by an external programmer for graphically illustrating a bridge demonstration.

FIG. 18A is a screenshot illustrating window 300 that user interface screen 120 presents when the user selects Demonstrate Bridge button 294. Window 300 includes text 302 that describes the bridge procedure as a "dose to deliver until previous drug is used up." Window 300 also includes timeline 310 and status indicator 304. Status indicator 304, in the example of FIG. 18, is an animated bar that moves across status indicator 304 in a fashion similar to status indicator 244 along timeline 245. In other examples, status indicator 304 may be a textual timer that counts down to zero, a textual timer that counts up to a specific time, a chart that has a fill percentage representative of the percent completion, or other indication of status of the bridge procedure.

In the example of FIG. 18A, window 300 also includes an animation of two fluids within IMD 12, a first fluid representation 316 corresponding to the old fluid and a second fluid representation 314 corresponding to the new fluid. In the example of FIG. 18A, first fluid representation 316 is a hashed box that represents the old fluid, and the second fluid representation 314 is a solid line. In other examples, the first fluid representation and the second fluid representation may be distinguished with different colors, different shading styles, different hatch marks, or other indicators.

As discussed above, a bridge procedure is used to replace an old fluid of IMD 12 with a new fluid. Therefore, window 300 depicts first fluid representation 316 as occupying less of IMD 12 and second fluid representation 314 as occupying more of IMD 12 as status indicator 304 progresses along timeline 310. That is, the respective representations of the old fluid and the new fluid are shown as moving through reservoir representation 206, internal tubing representation 208, catheter port representation 212, and catheter representation 214. Location bar 306 indicates the trailing end of the first fluid representation 316 for the old fluid and the leading end or beginning of the second fluid representation 314 for the new fluid. Hence, location bar 306 indicates the boundary between the old and new fluids. In some cases, if the old fluid had not been fully primed, an additional location bar may be provided at the distal-most, leading end of the first fluid representation 316 for the old fluid. User interface screen 120 displays movement of location bar 306 along graphical representations 208, 210, 212, and 214 as status indicator 304 moves along timeline 245. The animation of FIG. 18A may last a time much shorter than the actual time for a bridging phase of IMD 12, e.g., several seconds or several minutes. The user may also select Close button 308 at any time to close window 300.

Figure 18B:
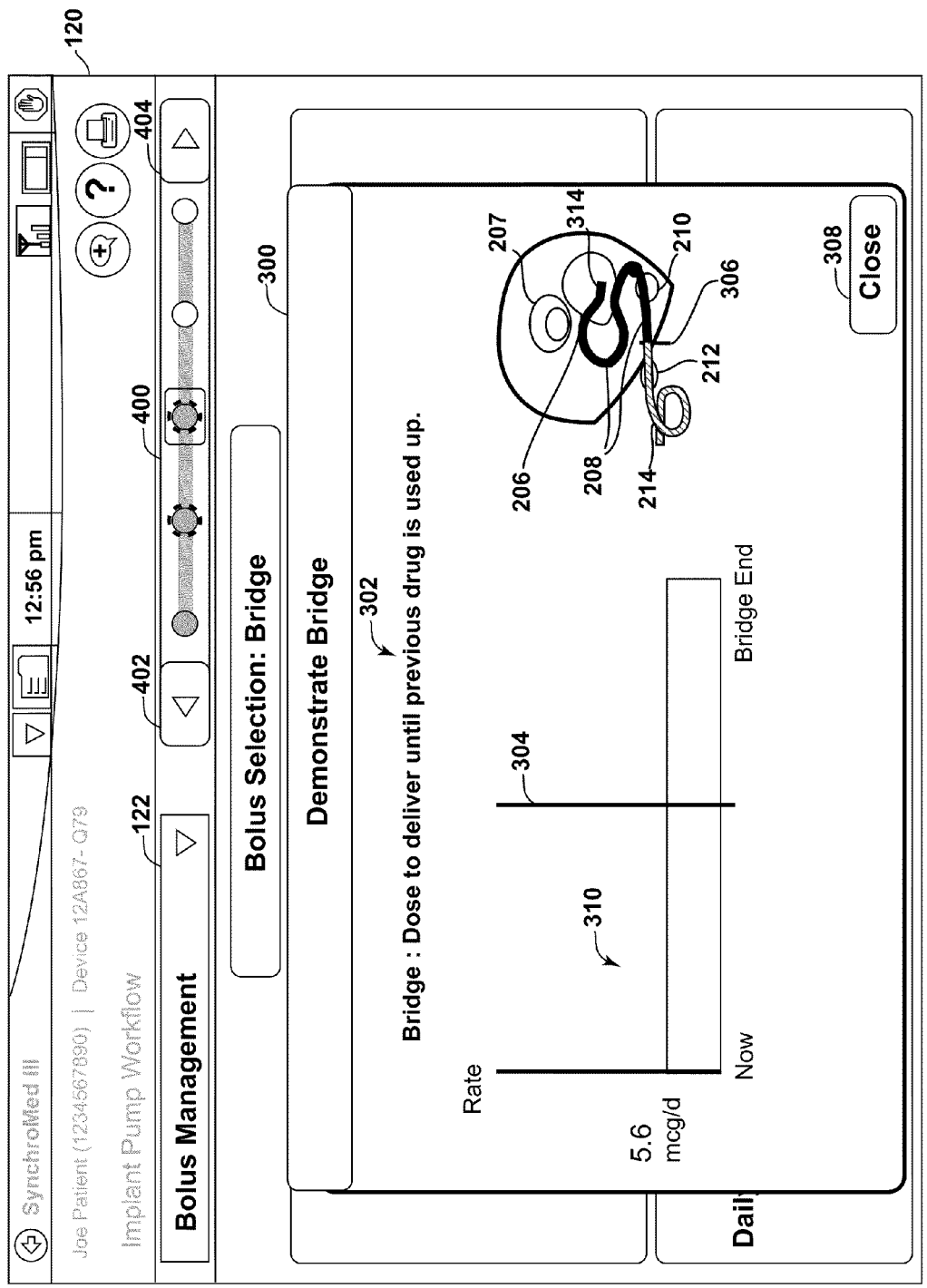

FIG. 18B is a screenshot of an example user interface presented by programmer 20 that indicates a status of a bridging phase of IMD 12. In the example of FIG. 18B, window 300 displays status indicator 304 approximately half-way across timeline 310. Similarly, window 300 displays first fluid representation 316 as occupying approximately half of the combined volume of catheter 18 and internal tubing 32, i.e., half-way through internal tubing representation 208 and catheter representation 214. Window 300 also displays second fluid representation 314 as occupying the other half of the combined volume of catheter 18 and internal tubing 32. Window 300 displays location bar 306 at the intersection of first fluid representation 316 and second fluid representation 314. In other examples, window 300 may display only fluid representations 314, 316, only location bar 306, or only status indicator 304.

Figure 19A:
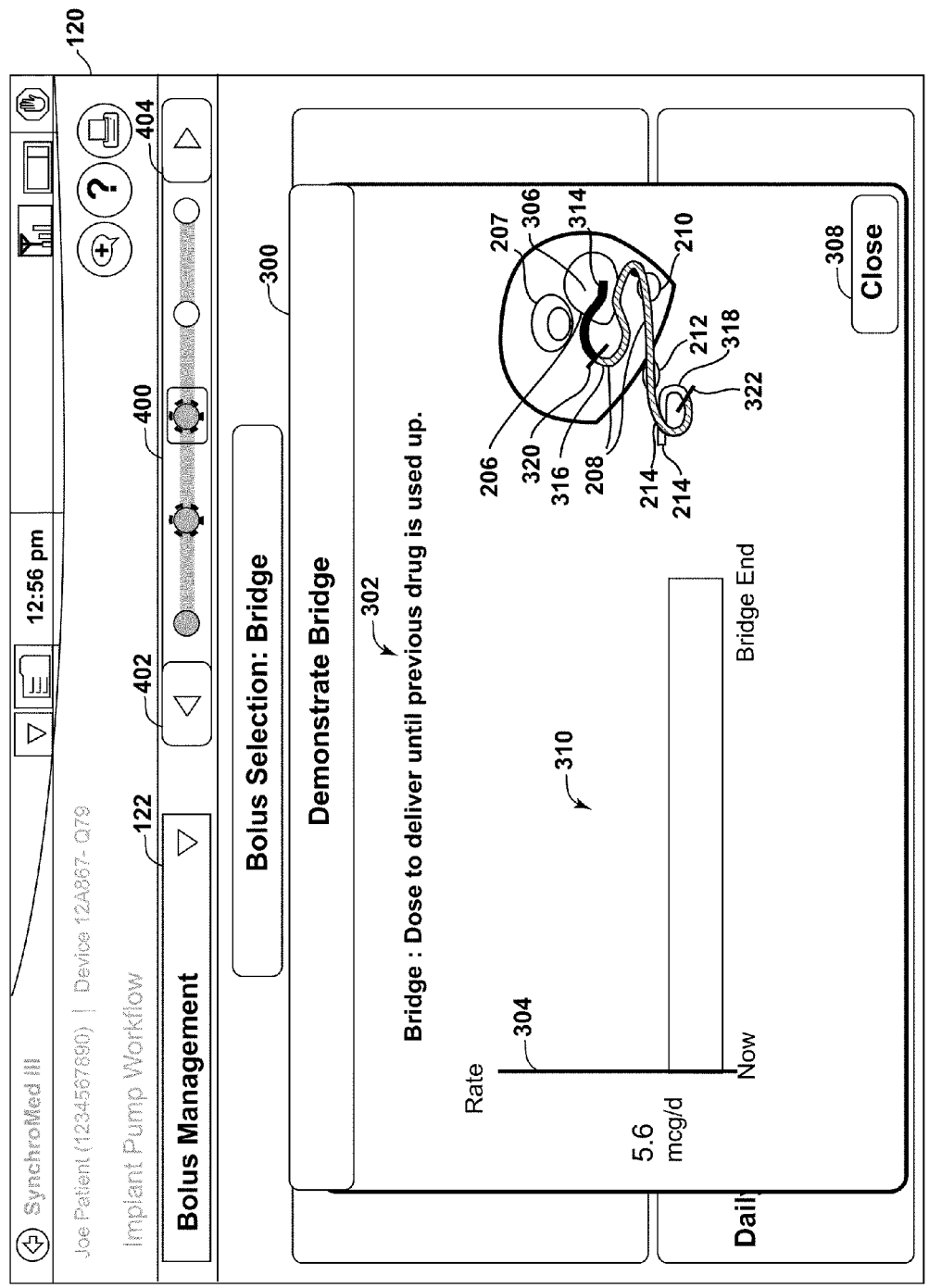
FIGS. 19A and 19B are screenshots illustrating an example user interface screen that presents two indications of two different fluids within an implantable fluid delivery device and an indication of a catheter segment that does not contain any fluid.
Figure 19B:
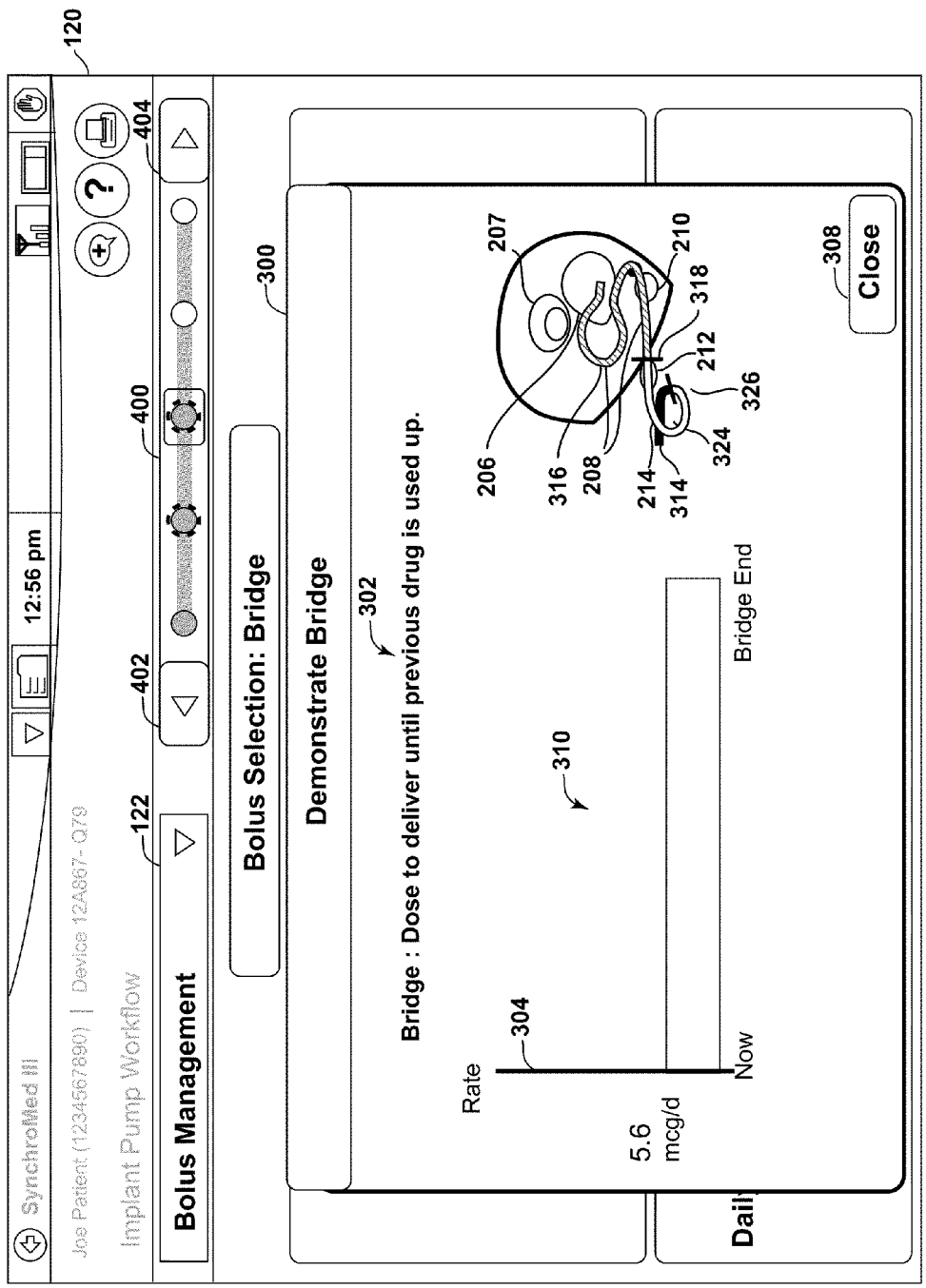

FIGS. 19A and 19B are screenshots illustrating an example user interface that presents two indications of two different fluids within IMD 12 and an indication of a catheter segment that does not contain any fluid. A clinician may split catheter 18 into multiple catheter segments, add segments, remove segments, or otherwise alter catheter 18. When a segment of catheter 18 is added or replaced, the new segment may not contain the fluid contained in reservoir 30 of IMD 12. The clinician may use a catheter joint to connect the two catheter segments together. The original segment of catheter 18 may still contain an old fluid. Programmer 20 may therefore program IMD 12 to perform a bridge to deliver the old fluid to patient 16 at a rate appropriate for the old fluid. Programmer 20 may also program IMD 12 to perform a prime when the new segment is added to the distal end of catheter 18.

FIG. 19A illustrates an example user interface that presents a distal catheter segment representation 318 that contains no fluid. User interface screen 120 may present representation 318 when a doctor has replaced a distal segment of catheter 18, i.e., a segment of catheter 18 that is most distant from IMD 12. In the example of FIG. 19A, user interface screen 120 displays a first fluid representation 316 and a second fluid representation 314. User interface screen 120 also displays marker 320 that indicates the point at which the first fluid ends and the second fluid begins, i.e., an intersection of the old fluid and the new fluid. User interface screen 120 also displays marker 322 that indicates where the first fluid begins and where no fluid is currently present, e.g., distal catheter segment representation 318. Programmer 20 may further recommend that a user of programmer 20 program a priming bolus to move the old fluid to the distal tip of the new catheter segment.

FIG. 19B illustrates an example user interface that presents a proximate catheter segment representation 324 that contains no fluid. User interface screen 120 may present representation 324 when a clinician has replaced a proximate segment of catheter 18, i.e., a segment of catheter 18 that is closest to IMD 12 and that interfaces with catheter access port 36. In this example, a gap between the old fluid and the new fluid occurs, which is represented by representation 324. User interface screen 120 also displays marker 326 that indicates the point at which the old fluid ends and the gap begins, and marker 328 that indicates the point at which the gap ends and the new fluid begins. Programmer 20 may further recommend that a user of programmer 20 program a bolus to move the new fluid to the point at which the old fluid ends.

Figure 20:
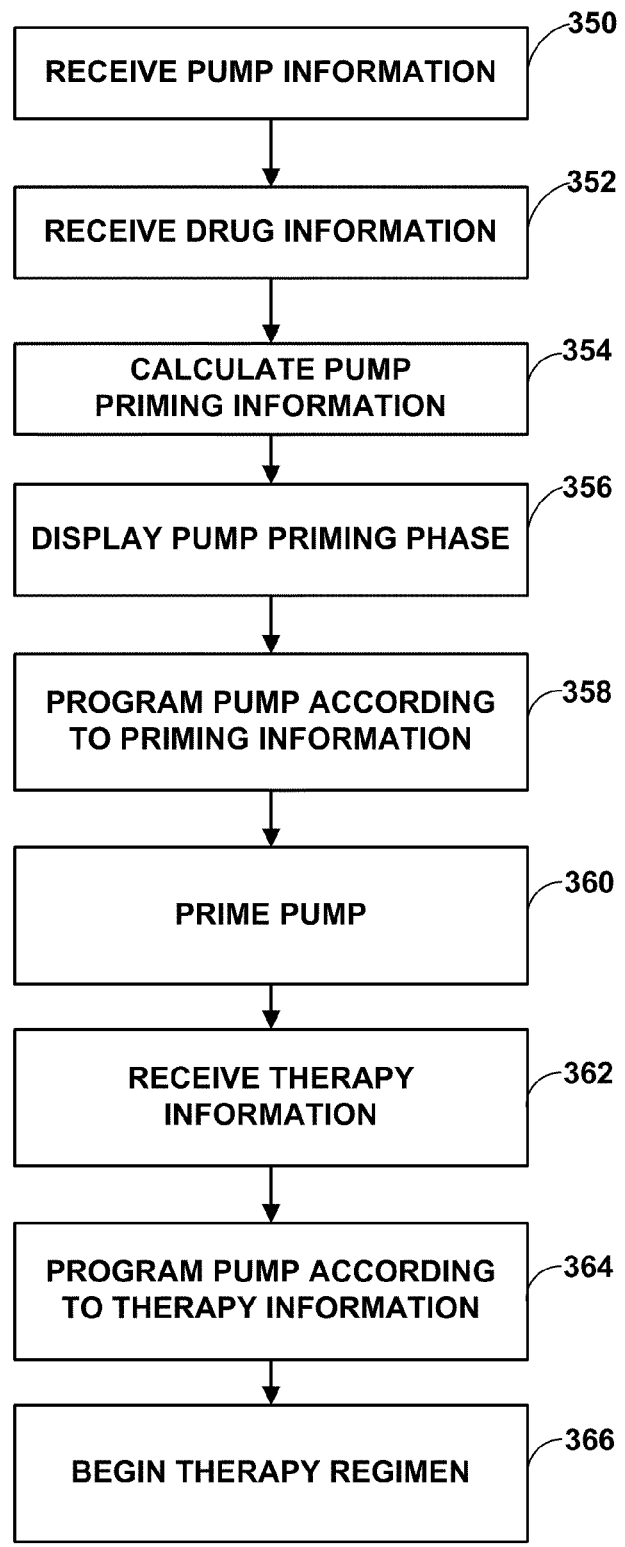
FIG. 20 is a flowchart illustrating an example method for receiving input from a user and programming an IMD according to user input received via a user interface presented by an external programmer.

FIG. 20 is a flowchart illustrating an example method for receiving input from a user and programming IMD 12 according to the user's input. Although described with respect to programmer 20, it should be understood that the method of FIG. 20 may be performed by any programmer device or any general device that interacts with an implantable medical device, such as IMD 12.

Initially, programmer 20 receives pump information 350 regarding IMD 12 (350). The pump information may include, for example, a reservoir volume, internal tubing volume, catheter volume, internal tubing length, internal tubing circumference, catheter length, catheter circumference, or other information. Factors such as internal tubing volume and catheter volume may either be received directly from a user or calculated from the length and volume information, e.g., by processor 84. In one example, programmer 20 may receive an identification of IMD 12 and retrieve the pump information, e.g., from a database indexed with the identification of IMD 12. Programmer 20 may receive the pump information from the user through a user interface, such as that depicted in FIG. 7.

Programmer 20 also receives drug information from the user (352). The drug information may include, for example, identifications of one or more drugs to be administered, respective concentrations for each of the identified drugs, or other information. Programmer 20 may, in one example, receive the drug information from the user with a user interface, such as that depicted in FIG. 8. In addition, programmer 20 receives a location of the drug and a location of IMD 12, e.g., with the user interface of FIG. 9.

Programmer 20 then calculates pump priming information according to the received pump information including a volume of the internal tubing of the pump and a volume of the catheter, the received drug information, and the received drug and pump locations (354). For example, programmer 20 may calculate, with processor 84, a volume of a priming bolus to move drug from its current location to the tip of catheter 18 of IMD 12. Programmer 20 may determine that the volume of the priming bolus is equal to the sum of the volumes of the internal tubing and the catheter. Memory 86 may store one or more functions, modules, procedures, or other means for performing the calculations, executed by processor 84.

Programmer 20 then displays, with user interface 82, a pump priming phase animation, e.g., as discussed with respect to FIGS. 12A-12C (356). Programmer 20 may display, for example, a representation of progress of the priming phase of IMD 12, a representation of a portion of IMD 12, and an indication of a location of fluid within IMD 12. In general, the representation of the location of the fluid is overlayed with the representation of the portion of IMD 12. The representation of the location of the fluid is also determined as a function of time, corresponding to the representation of progress of the priming phase. That is, as the priming phase progresses, the representation of the location of the fluid progresses along the representation of IMD 12.

Programmer 20 may program IMD 12 with the priming information (358). In one example, programmer 20 may first receive an indication from the user that the priming information is correct before programming IMD 12. When the priming information is not correct, programmer 20 first receives new priming information before programming IMD 12 and then programs IMD 12 with the new priming information.

Once programmer 20 has programmed IMD 12, programmer 20 causes IMD 12 to begin the priming phase (360). Alternatively, the priming phase may be simulated. In one example, programmer 20 displays a representation of the actual priming phase with user interface 82 to a user. Programmer 20 may also display a time until priming is finished to the user.

Programmer 20 also receives therapy information for a therapy to be administered to patient 16 by IMD 12 (362). The user may enter, for example, a dose of fluid to be administered, an amount of drug to be administered, a time over which the drug/fluid is to be administered, or other factors. Programmer 20 then programs IMD 20 in accordance with the therapy program information (364) and causes IMD 20 to administer a therapy regimen (366) in accordance with the therapy program information once the priming phase of IMD 20 has finished.

Figure 21:
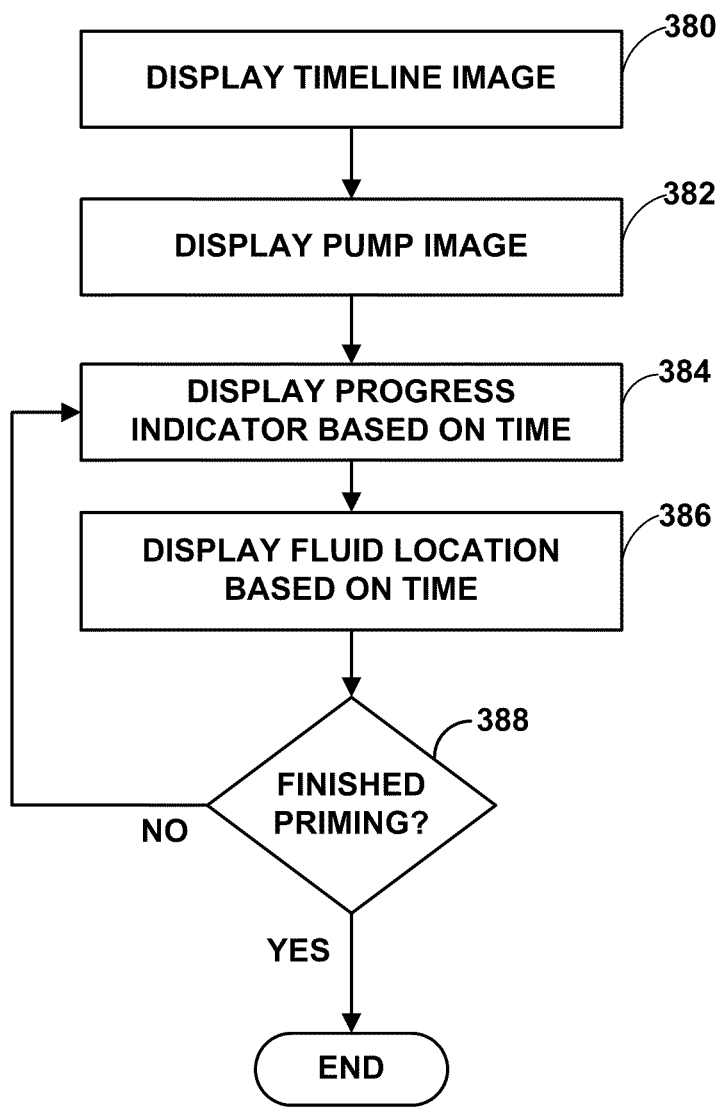
FIG. 21 is a flowchart illustrating an example method for displaying a pump priming phase via a user interface presented by an external programmer.

FIG. 21 is a flowchart illustrating an example method for displaying a representation of an implantable fluid delivery device priming phase. Initially, user interface 82 of programmer 20 presents an image of timeline 245 (380) and a representation of a portion of IMD 12 (382). User interface 82 then displays status indicator 244 along timeline 245 as a function of time (384). User interface 82 also displays fluid location indicator 246 along the representation of IMD 12 as a function of time (386). Programmer 20 then determines whether the priming phase of IMD 12 (or a simulated priming phase of IMD 12) has finished (388). Programmer 20 updates user interface 82 with new locations of status indicator 244 and fluid location indicator 246 as a function of time until the priming phase has finished. It should be understood that processor 84 of programmer 20 causes status indicator 244 to move in parallel with fluid location indicator 246 as time progresses. That is, although illustrated as two separate steps, in one example, the two steps may be performed in parallel such that user interface 82 of programmer 20 illustrates the progress of the priming phase while simultaneously illustrating the location of the fluid corresponding to the progress of the priming phase.

Figure 22:
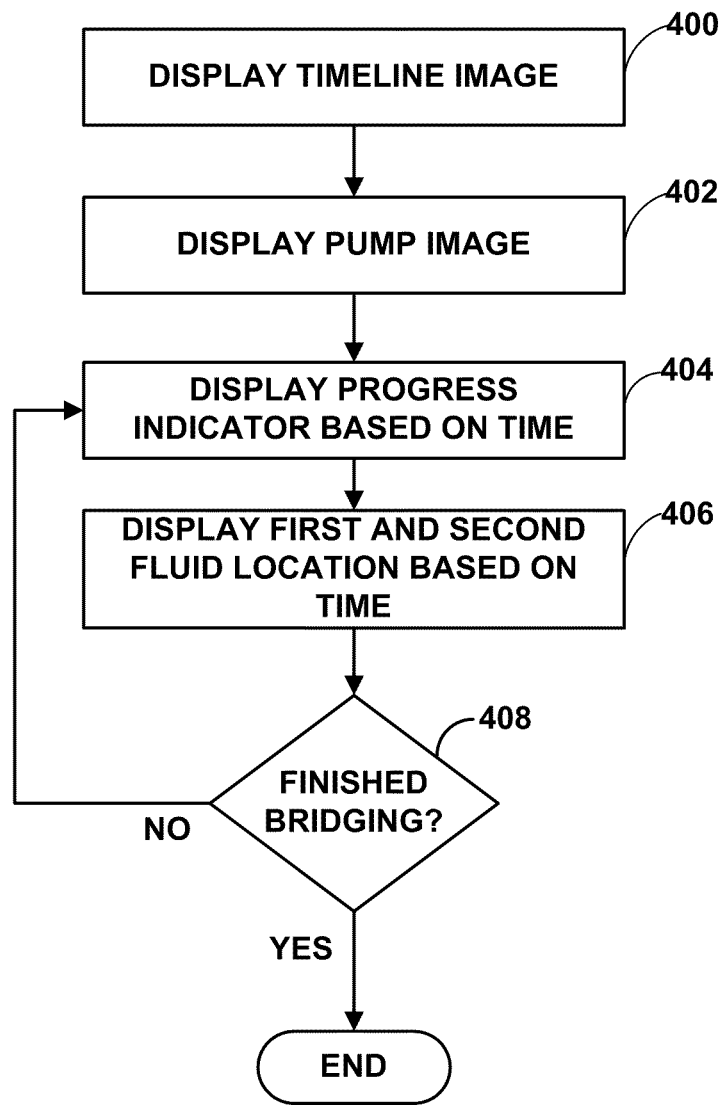
FIG. 22 is a flowchart illustrating an example method for displaying a pump bridging phase via a user interface presented by an external programmer.

FIG. 22 is a flowchart illustrating an example method for displaying a representation of an implantable fluid delivery device bridging phase. Initially, user interface 82 of programmer 20 presents an image of timeline 310 (400) and a representation of at least a portion of IMD 12 (402). User interface 82 then displays status indicator 304 along timeline 245 as a function of time (404). User interface 82 also displays first fluid representation 316 and second fluid representation 314 at their respective locations with the representation of IMD 12 as a function of time (406). In one example, user interface 82 also displays location bar 306 at the intersection of first fluid representation 316 and second fluid representation 314. Programmer 20 then determines whether the bridging phase of IMD 12 (or a simulated bridging phase of IMD 12) has finished (408). Programmer 20 updates user interface 82 with new locations of status indicator 244 and fluid location indicator 246 as a function of time until the priming phase has finished.

Figure 23A:
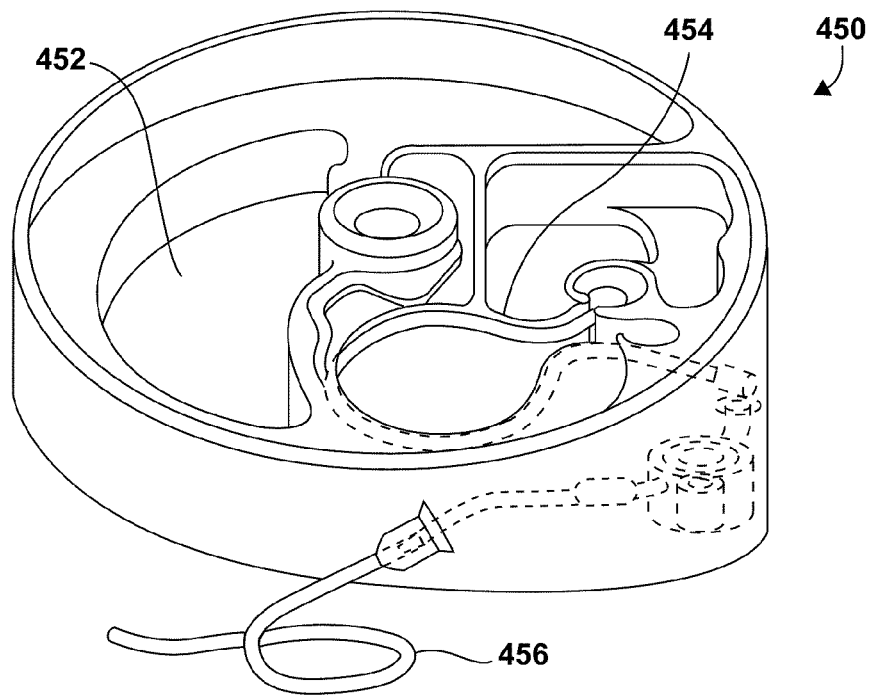
FIGS. 23A-23F are screenshots illustrating alternative views of a representation of an implantable fluid delivery device.
Figure 23B:
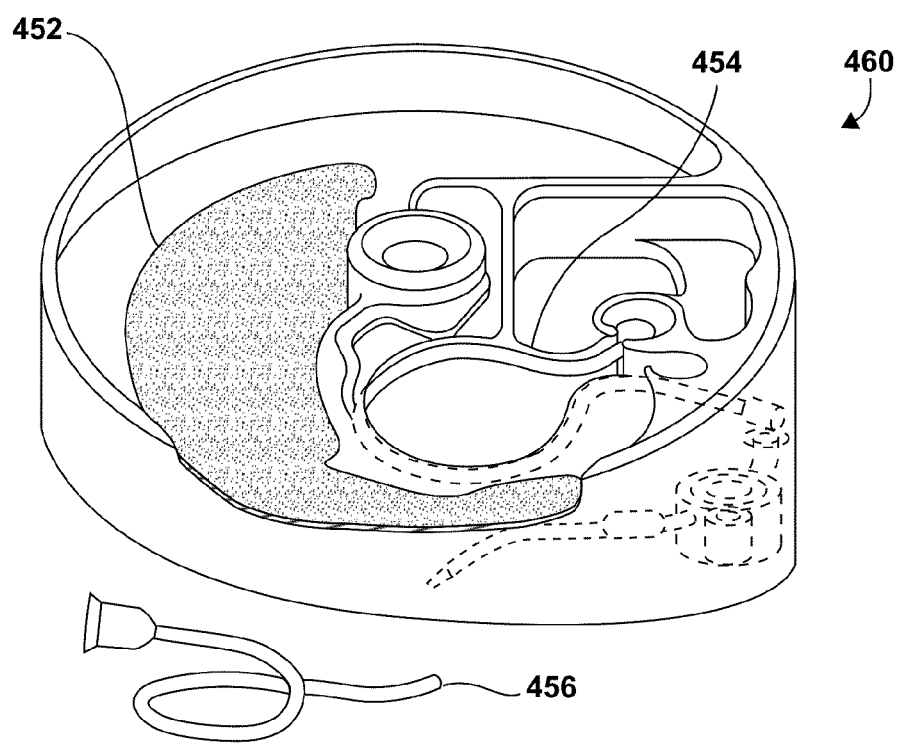

FIGS. 23A-23F are screenshots illustrating alternative views of a representation of an implantable fluid delivery device. Each of FIGS. 23A-23F depicts a representation of, for example, IMD 12 that includes reservoir representation 452, internal tubing representation 454, and catheter representation 456. The illustrations of FIGS. 23A-23F may correspond to graphical representation 204, e.g., of FIG. 9 and/or FIG. 12. FIG. 23A depicts implantable fluid delivery device representation 450 that depicts each of reservoir representation 452, internal tubing representation 454, and catheter representation 456 as being empty, i.e., not containing a fluid. Implantable fluid delivery device representation 450 may correspond to a time at which no fluid has been inserted into IMD 12 and catheter 18, e.g., before IMD 12 has been implanted. FIG. 23B depicts implantable fluid delivery device representation 458 that depicts internal tubing representation 454 and catheter representation 456 as being empty, but reservoir representation 452 as containing fluid by shading reservoir representation 452. In other examples, other means for representing presence of a fluid may be used, e.g., hatching, outlining, a flashing fill, a different color, color vs. grayscale (where gray represents no fluid, color represents presence of fluid), or other visual depictions. FIG. 23B may correspond to a time at which fluid has first been inserted into reservoir 30 of IMD 12 and IMD 12 has not yet been primed.

Figure 23C:
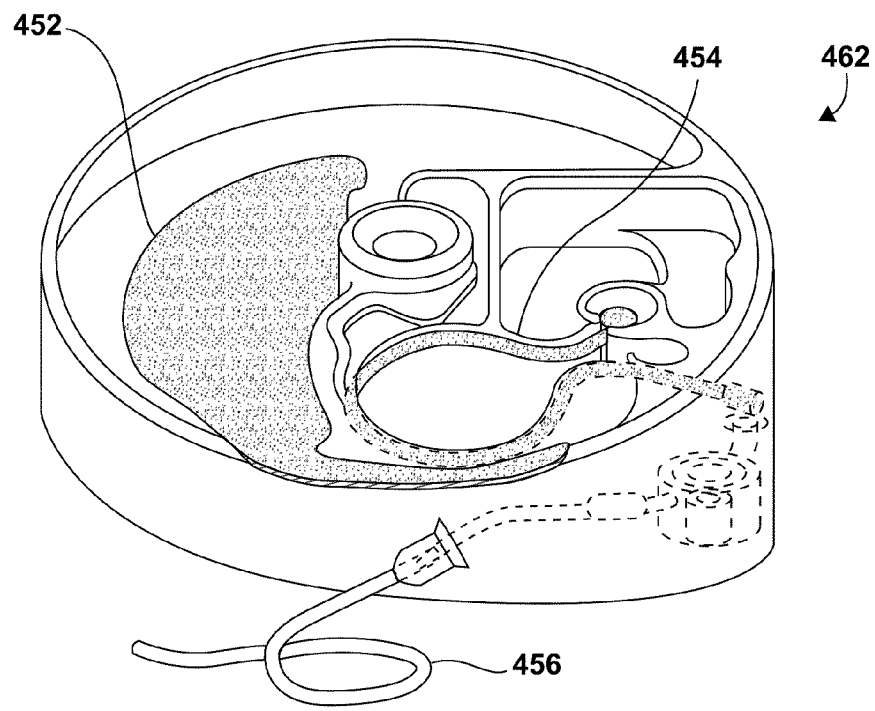
Figure 23D:
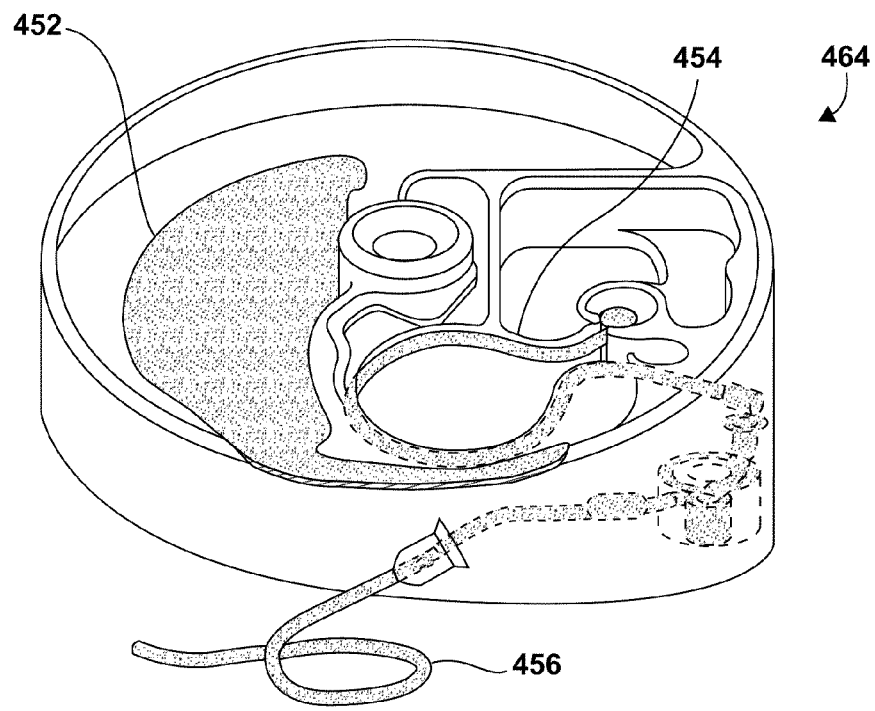
Figure 23E:
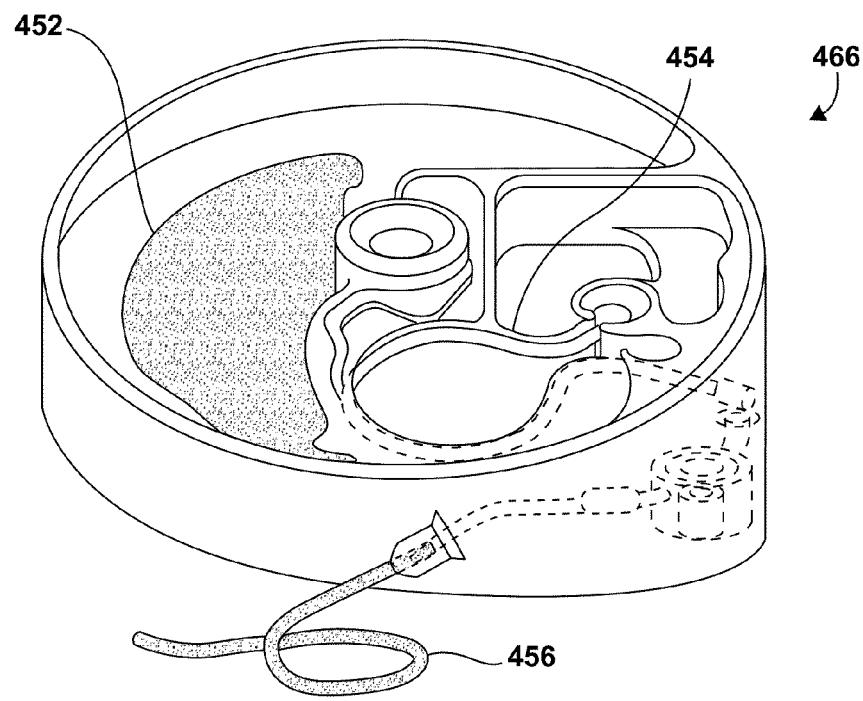
Figure 23F:
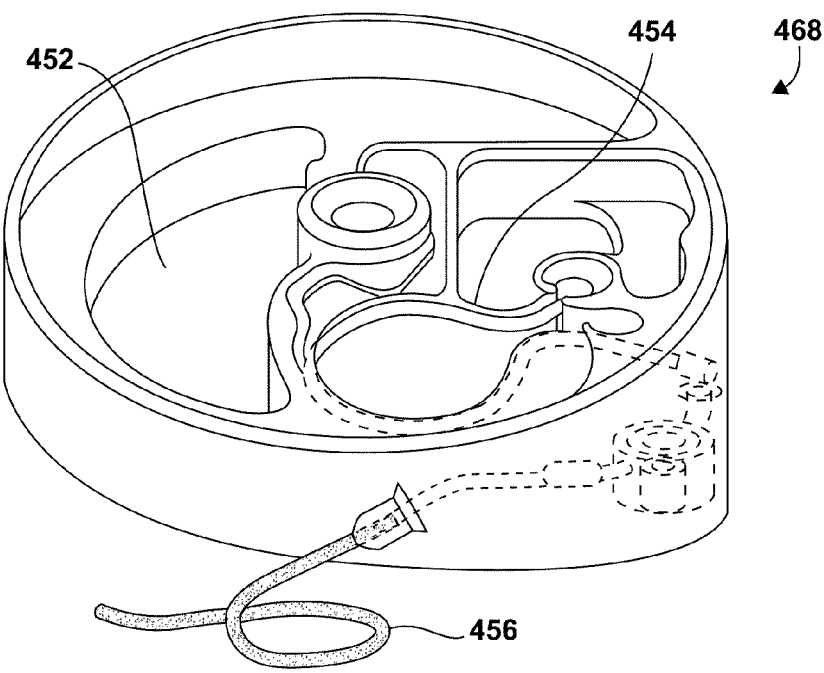

FIG. 23C depicts implantable fluid delivery device representation 462 that depicts reservoir representation 452 and internal tubing representation 454 as containing fluid, and catheter representation 456 as being empty. FIG. 23C may correspond to a pre-implant prime of IMD 12, where fluid has been pushed through internal tubing 32 but has not yet reached catheter 18. FIG. 23D depicts implantable fluid delivery device representation 464 that depicts each of reservoir representation 452, internal tubing representation 454, and catheter representation 456 as containing fluid. FIG. 23D may correspond to a point immediately following a priming phase of IMD 12, where the priming phase has caused fluid to reach the distal tip of catheter 18. FIG. 23E depicts implantable fluid delivery device representation 466 that depicts reservoir representation 452 and catheter representation 456 as containing fluid but internal tubing representation 454 as being empty. FIG. 23E may correspond to a situation in which programmer 20 should program a bridge procedure for IMD 12, e.g., catheter 18 may contain a first fluid and reservoir 30 may contain a second fluid. Alternatively, FIG. 23E may correspond to a situation in which catheter 18 has been transferred from a first IMD to a replacement IMD that has received fluid, but has not delivered fluid to catheter access port 36. FIG. 23F depicts implantable fluid delivery device representation 468 that depicts reservoir representation 452 and internal tubing representation 454 as being empty and catheter representation 456 as containing fluid. FIG. 23F may correspond to a situation in which catheter 18 has been transferred from a first IMD to a replacement IMD that has not yet received a fluid.

The techniques described herein may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described herein may also be embodied in a computer-readable medium, such as a computer-readable storage medium, containing instructions. Instructions embedded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
 displaying a graphical illustration representative of structure of a portion of an implantable fluid delivery device via a user interface associated with a programmer device that communicates with the implantable fluid delivery device; and
 displaying, as part of the graphical illustration, an indication of a location of an endpoint of a fluid within the implantable fluid delivery device at a particular time during progression of a delivery phase via the user interface, wherein the endpoint comprises a graphical representation of a point in the implantable fluid delivery device distinguishing where the fluid is present from where the fluid is not present in the implantable fluid delivery device.

2. The method of claim 1, further comprising displaying a graphical illustration representative of progress of the delivery phase of the implantable fluid delivery device.

3. The method of claim 1, wherein displaying the indication of the location of the endpoint of the fluid within the implantable fluid delivery device at a particular time during progression of the delivery phase comprises displaying the indication of the location of the endpoint of the fluid within the implantable fluid delivery device during an actual delivery phase of the implantable fluid delivery device.

4. The method of claim 1, wherein displaying the indication of the location of the endpoint of the fluid within the implantable fluid delivery device at a particular time during progression of the delivery phase comprises displaying the indication of the location of the endpoint of the fluid within the implantable fluid delivery device during a simulation of the delivery phase of the implantable fluid delivery device.

5. The method of claim 1, wherein displaying the graphical illustration representative of structure of the portion of the implantable fluid delivery device comprises:
 displaying a graphical illustration representative of structure of a reservoir of the implantable fluid delivery device;
 displaying a graphical illustration representative of structure of internal tubing of the implantable fluid delivery device; and
 displaying a graphical illustration representative of structure of a catheter of the implantable fluid delivery device.

6. The method of claim 5, wherein displaying the indication of the location of the endpoint of the fluid within the implantable fluid delivery device comprises displaying the indication of the location of the endpoint of the fluid within the internal tubing.

7. The method of claim 5, wherein displaying the indication of the location of the endpoint of the fluid within the implantable fluid delivery device comprises displaying the indication of the location of the endpoint of the fluid within the catheter.

8. The method of claim 1, wherein displaying the indication of the location of the endpoint of the fluid within the implantable fluid delivery device comprises displaying the indication over the displayed graphical illustration representative of structure of the portion of the implantable fluid delivery device.

9. The method of claim 1, wherein the delivery phase comprises a priming phase of the implantable fluid delivery device.

10. The method of claim 1, wherein the delivery phase comprises a bridging phase of the implantable fluid delivery device.

11. The method of claim 10, wherein the fluid comprises a first fluid and the indication comprises a first indication, the method further comprising displaying, as part of the graphical illustration, a second indication of a second location of a second fluid within the implantable fluid delivery device.

12. The method of claim 11, further comprising displaying an indication of a gap between the first indication of the location of the endpoint of the first fluid and the second indication of the second location of the second fluid.

13. A programmer device comprising:
 a device interface that communicates with an implantable fluid delivery device; and
 a user interface that displays a graphical illustration representative of structure of a portion of the implantable fluid delivery device and displays, as a part of the graphical illustration, an indication of a location of an endpoint of a fluid within the implantable fluid delivery device at a particular time during progression of a delivery phase of the implantable fluid delivery device, wherein the endpoint comprises a graphical representation of a point in the implantable fluid delivery device distinguishing where the fluid is present from where the fluid is not present in the implantable fluid delivery device.

14. The programmer device of claim 13, wherein the user interface displays a graphical illustration representative of progress of the delivery phase of the implantable fluid delivery device.

15. The programmer device of claim 13, wherein the user interface displays the indication of the location of the endpoint of the fluid within the implantable fluid delivery device during a simulation of the delivery phase of the implantable fluid delivery device.

16. The programmer device of claim 13, wherein the graphical illustration representative of structure of a portion of the implantable fluid delivery device displayed by the user interface comprises a graphical illustration of structure of a reservoir, internal tubing, and a catheter of the implantable fluid delivery device.

17. The programmer device of claim 16, wherein the user interface displays the indication of the location of the endpoint of the fluid within the internal tubing.

18. The programmer device of claim 16, wherein the user interface displays the indication of the location of the endpoint of the fluid within the catheter.

19. The programmer device of claim 13, wherein the delivery phase comprises a bridging phase, wherein the fluid comprises a first fluid, wherein the indication comprises a first indication, and wherein the user interface displays, as a part of the graphical illustration, a second indication of a second location of a second fluid.

20. A system comprising:
an implantable fluid delivery device that delivers a fluid to a patient; and
a programmer device, communicatively coupled to the implantable fluid delivery device, that displays a graphical illustration representative of structure of a portion of the implantable fluid delivery device and displays, as a part of the graphical illustration, an indication of a location of an endpoint of a fluid within the implantable fluid delivery device at a particular time during progression of a delivery phase of the implantable fluid delivery device, wherein the endpoint comprises a graphical representation of a point in the implantable fluid delivery device distinguishing where the fluid is present from where the fluid is not present in the implantable fluid delivery device.

21. The system of claim 20, wherein the programmer device displays a graphical illustration representative of progress of the delivery phase of the implantable fluid delivery device.

22. The system of claim 20, wherein the programmer device displays the indication of the location of the endpoint of the fluid during a simulation of the delivery phase of the implantable fluid delivery device.

23. The system of claim 20, wherein the graphical illustration representative of structure of the portion of the implantable fluid delivery device displayed by the programmer device comprises a graphical illustration representative of structure of a reservoir, internal tubing, and a catheter of the implantable fluid delivery device.

24. The system of claim 23, wherein the programmer device displays the indication of the location of the endpoint of the fluid within the internal tubing.

25. The system of claim 23, wherein the programmer device displays the indication of the location of the endpoint of the fluid within the catheter.

26. The system of claim 20, wherein the delivery phase comprises a bridging phase, wherein the fluid comprises a first fluid, wherein the indication comprises a first indication, and wherein the programmer device displays, as a part of the graphical illustration, a second indication of a second location of a second fluid within the implantable fluid delivery device.

27. A non-transitory computer-readable medium comprising instructions for causing a programmable processor to:
display a graphical illustration representative of structure of a portion of an implantable fluid delivery device; and
display, as a part of the graphical illustration, an indication of a location of an endpoint of a fluid within the implantable fluid delivery device at a particular time during progression of a delivery phase of the implantable fluid delivery device, wherein the endpoint comprises a graphical representation of a point in the implantable fluid delivery device distinguishing where the fluid is present from where the fluid is not present in the implantable fluid delivery device.

28. The non-transitory computer-readable medium of claim 27, further comprising instructions to display a graphical illustration representative of progress of the delivery phase of the implantable fluid delivery device.

29. The non-transitory computer-readable medium of claim 27, wherein the instructions to display the indication of the location of the endpoint of the fluid within the implantable fluid delivery device during the delivery phase comprise instructions to display the indication of the location of the endpoint of the fluid within the implantable fluid delivery device during an actual delivery phase of the implantable fluid delivery device.

30. The non-transitory computer-readable medium of claim 28, wherein the instructions to display the graphical illustration representative of progress of the delivery phase comprise instructions to display the graphical illustration representative of progress of the delivery phase as a simulation of the delivery phase of the implantable fluid delivery device.

31. The non-transitory computer-readable medium of claim 27, wherein the instructions to display the graphical illustration representative of structure of the portion of the implantable fluid delivery device comprise instructions to:
display a graphical illustration representative of structure of a reservoir of the implantable fluid delivery device;
display a graphical illustration representative of structure of internal tubing of the implantable fluid delivery device; and
display a graphical illustration representative of structure of a catheter of the implantable fluid delivery device.

32. The non-transitory computer-readable medium of claim 31, wherein the instructions to display the indication of the location of the endpoint of the fluid within the implantable fluid delivery device comprise instructions to display the indication of the location of the endpoint of the fluid within the internal tubing.

33. The non-transitory computer-readable medium of claim 31, wherein the instructions to display the indication of the location of the endpoint of the fluid within the implantable fluid delivery device comprise instructions to display the indication of the location of the endpoint of the fluid within the catheter.

34. The non-transitory computer-readable medium of claim 27, wherein the delivery phase comprises a bridging phase, wherein the fluid comprises a first fluid, wherein the indication comprises a first indication, further comprising instructions to display, as a part of the graphical illustration, a second indication of a second location of a second fluid within the implantable fluid delivery device.

35. A device comprising:
means for communicating with an implantable fluid delivery device;
means for displaying a graphical illustration representative of structure of a portion of the implantable fluid delivery device; and
means for displaying, as a part of the graphical illustration, an indication of a location of an endpoint of a fluid within the implantable fluid delivery device at a particular time during progression of a delivery phase of the implantable fluid delivery device, wherein the endpoint comprises a graphical representation of a point in the implantable fluid delivery device distinguishing where the fluid is present from where the fluid is not present in the implantable fluid delivery device.

36. The device of claim 35, further comprising means for displaying a graphical illustration representative of progress of the delivery phase of the implantable fluid delivery device.

37. The device of claim 35, wherein the means for displaying the indication of the location of the endpoint of the fluid within the implantable fluid delivery device comprise means for displaying the indication of the location of the endpoint of the fluid within the implantable fluid delivery device as a simulation of the delivery phase of the implantable fluid delivery device.

38. The device of claim 35, wherein the means for displaying the graphical illustration representative of structure of the portion of the implantable fluid delivery device comprise:

means for displaying a graphical illustration representative of structure of a reservoir of the implantable fluid delivery device;

means for displaying a graphical illustration representative of structure of internal tubing of the implantable fluid delivery device; and means for displaying a graphical illustration representative of structure of a catheter of the implantable fluid delivery device.

39. The device of claim 38, wherein the means for displaying the indication of the location of the endpoint of the fluid within the implantable fluid delivery device comprise means for displaying the indication of the location of the endpoint of the fluid within the internal tubing.

40. The device of claim 38, wherein the means for displaying the indication of the location of the endpoint of the fluid within the implantable fluid delivery device comprise means for displaying the indication of the location of the endpoint of the fluid within the catheter.

41. The device of claim 35, wherein the delivery phase comprises a bridging phase, wherein the fluid comprises a first fluid, wherein the indication comprises a first indication, further comprising means for displaying, as a part of the graphical illustration a second indication of a second location of a second fluid within the implantable fluid delivery device.

42. The method of claim 1, wherein displaying the graphical illustration representative of structure of the portion of the implantable fluid delivery device via the user interface comprises displaying a pictorial representation of the portion of the implantable fluid delivery device via the user interface, and wherein displaying the indication of the location of the endpoint of the fluid within the implantable fluid delivery device comprises displaying an indication of a first location of fluid from a plurality of possible locations of fluid within the implantable fluid delivery device.

43. The programmer device of claim 13, wherein the user interface displays a pictorial representation of the portion of the implantable fluid delivery device via the user interface and displays an indication of a first location of fluid from a plurality of possible locations of fluid within the implantable fluid delivery device.

44. The system of claim 20, wherein the programmer device displays a pictorial representation of the portion of the implantable fluid delivery device and displays an indication of a first location of fluid from a plurality of possible locations of fluid within the implantable fluid delivery device.

45. The non-transitory computer-readable medium of claim 27, wherein the instructions for causing the programmable processor to display the graphical illustration representative of structure of the portion of the implantable fluid delivery device cause the programmable processor to display a pictorial representation of the portion of the implantable fluid delivery device, and wherein the instructions for causing the programmable processor to display an indication of a location of the endpoint of the fluid within the implantable fluid delivery device at a particular time during progression of a delivery phase of the implantable fluid delivery device cause the programmable processor to display an indication of a first location of fluid from a plurality of possible locations of fluid within the implantable fluid delivery device.

46. The system of claim 35, wherein the means for displaying the graphical illustration representative of structure of the portion of the implantable fluid delivery device comprise means for displaying a pictorial representation of the portion of the implantable fluid delivery device via the user interface, and wherein the means for displaying the indication of the location of the endpoint of the fluid within the implantable fluid delivery device comprise means for displaying an indication of a first location of fluid from a plurality of possible locations of fluid within the implantable fluid delivery device.

* * * * *